United States Patent [19]

Reddy et al.

[11] Patent Number: 5,648,213
[45] Date of Patent: Jul. 15, 1997

[54] COMPOSITIONS AND METHODS FOR USE IN DETECTION OF ANALYTES

[75] Inventors: M. Parameswara Reddy, Brea; James C. Sternberg, Fullerton, both of Calif.

[73] Assignee: Beckman Instruments, Inc., Fullerton, Calif.

[21] Appl. No.: 298,523

[22] Filed: Aug. 30, 1994

[51] Int. Cl.$^6$ .................. C12Q 1/68; G01N 33/53; G01N 33/574; C07H 21/02
[52] U.S. Cl. .................. 435/6; 435/7.1; 435/7.23; 436/538; 536/23.1
[58] Field of Search .................. 435/6, 7.1; 436/538; 536/23.1

[56] References Cited

U.S. PATENT DOCUMENTS

| | | | |
|---|---|---|---|
| 4,650,675 | 3/1987 | Borel et al. | 424/130.1 |
| 5,391,723 | 2/1995 | Priest | 536/23.1 |

FOREIGN PATENT DOCUMENTS

| | | | |
|---|---|---|---|
| 0544212A1 | 2/1993 | European Pat. Off. | C12Q 1/68 |
| WO93/15229 | 5/1993 | WIPO | C12Q 1/68 |

OTHER PUBLICATIONS

"Heterobifunctional Cross–Linkers", Chemistry of Protein Conjugation and Crosslinking; Wang, S.S.; (1991) CRC Press, pp. 147–164.
Hanvey, Jeffery, C., et al; "Antisense and Antigene Properties of Peptide Nucleic Acids"; Science, vol. 258; 27 Nov. 1992, pp. 1481–1485.
Buchardt, Ole, et al; "Peptide Nucleic Acids and Their Potential Applications in Biotechnology"; Tibtech, vol. 11, Sep. 1993; pp. 384–386.
Fourrey, Jean–Louis, et al; "Improved Procedure for the Preparation of Deoxynucleoside Phosphoramidites: Arylphosphoramidites as New Convenient Intermediates for Oligodeoxynucleotide Synthesis", Tetrahedron Letters, vol. 25, No. 40, pp. 4511–4514, 1984.
Pon, Richard T., "Enhanced Coupling Efficency Using 4–Dimethylaminopyridine (DMAP) and Either Tetrazole, 5–(o–Nitrophenyl) Tetrazole, or 5–(p–Nitrophenyl) Tetrazole in the Solid Phase Synthesis of Oligoribonucleotides by the Phosphoramidite Procedure", Tetrahedron Letters, vol. 28, No. 32, pp. 3643–3646, 1987.
Froehler, B. C., "Substituted 5–Phenyltertrazoles: Improved Activators of Deoxynucleos IDI Phosphoramidites in Deoxyligonucleotide Synthesis"; Tetrahedron Letters, vol. 24, No. 31, pp. 3171–3174, 1983.
Stee, Wojiciech, J. et al; "Stereochemical Studies of the Formation of Chiral Internucleotide Linkages by Phosphoramidite Coupling in the Synthesis of Oligodeoxyribonucleotides"; Tetrahedron Letters, vol. 25, No. 46, pp. 5279–5282, 1984.
Beaucate, S. L., et al; "Synthesis of oligonucleotides";Tetrahedron, vol. 48 (1992) pp. 2290–2291.

Berner, S., et al; "The Reaction of Tetrazole with Phosphoramidites as a Model for the Nucleotide Coupling Step;" Nucleosides & Nucleotides, 7(5&6), pp. 673–767 (1988).
Köster, H. et al; "Some Improvements of Polymer Oligoneoxynucleotide Synthesis"; Natural Products Chemistry (1984), pp. 227–237.
Hering G., et al; "Preparation and Properties of Chloro–N, N–dialkylamino–2,2,2–trichloroethoxy and Chloro–N, N–dialkylamino–2,2,2–trichloro–1, 1–dimethylethoxyphosphines and thier Deoxynucleoside Phosphiteamidates"; Nucleosides & Nucleotides , 4(1&2), pp. 169–171 (1985).
Wright, Peter, et al; "Large Scale Synthesis of Oligonucleotides via Phosphoramidte Nucleosides and a High–Loaded Polystyrene Support", Tetrahedron Letters, vol. 34, No. 21, pp. 3373–3376 (1993).
Fourrey, J. L., et al; "A New Method For The Synthesis of Branched Ribonucleotides"; Tahedron letters, vol. 28, No. 16, pp. 1769–1772, 1987.
Arnold, Luboš, et al; "Automated Chloridite and Amidite Synthesis of Oligodeoxyribonucleotides on a Long Chain Support Using Amidine Protected Purine Nucleosides", Collect. Czech, Chem. Commun. (Vol. 54, 487 (1989) pp. 523–533.
Wolter, A., et al; "Polymer Support Oligonucleotide Synthesis XX$^1$ : Synthesis of a Henhectacosa Deoxynucleotide By Use of a Dimeric Phosphoramidite Synthon"; Nucleosides & Nucleotides, 5(1), pp. 65–77 (1986).

*Primary Examiner*—Lila Feisee
*Assistant Examiner*—Yvonne Eyler
*Attorney, Agent, or Firm*—William H. May; Janis C. Henry

[57] ABSTRACT

Double stranded nucleic acid duplexes serve as universal harvestable and cleavable link systems in a variety of different types of immunoassays (e.g., sandwich, competitive, etc.). Depending upon the type of assay, at least one specific component involved in the assay system is attached to a first member of a pair of sequences forming a double stranded nucleic acid (i.e., two oligonucleotides comprising substantially complementary sequences). The assay is carried out in the presence of a support to which is attached an oligonucleotide which is the other member of the pair of sequences forming a double-stranded nucleic acid duplex under hybridization conditions. Upon the hybridization of the two complementary oligonucleotides to form a duplex, the component of the assay system to which the first member of the pair of oligonucleotides is attached may thereby be effectively removed from the solution phase and harvested onto the support. Oligonucleotides bound to a support are reusable in multiple successive assays. Moreover, any given support-bound oligonucleotide can be used in accordance with the present invention for the analysis of a variety of different analytes. In many cases, the assay system includes a label to facilitate quantifying the amount of analyte; in others, the amount of analyte may be determined without the use of any extraneous label.

25 Claims, No Drawings ns, there are nonetheless significant disadvantages with the heretofore-known assay systems. -->

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear (i i) MOLECULE TYPE: DNA (genomic)

(x i) SEQUENCE DESCRIPTION: SEQ ID NO:1:

CAAAATACGT GGCCTTATGG TTACAG 26

(2) INFORMATION FOR SEQ ID NO:2:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:2:

AAGGCCACGT ATTTTGCAAG CTATTTAACT 30

(2) INFORMATION FOR SEQ ID NO:3:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:3:

AGTTAAATAG CTTGCAAAAT ACGTGGCCTT 30

(2) INFORMATION FOR SEQ ID NO:4:

(i) SEQUENCE CHARACTERISTICS:
  (A) LENGTH: 26 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:4:

CATCGCCAGT CAGTATTCTC GGAGCA 26

(2) INFORMATION FOR SEQ ID NO:5:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:5:

ATACTGACTG GCGATGCTGT CGAAGTAGCG 30

(2) INFORMATION FOR SEQ ID NO:6:

(i) SEQUENCE CHARACTERISTICS:
  (A) LENGTH: 30 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:6:

CGCTACTTCG ACAGCATCGC CAGTCAGTAT 30

( 2 ) INFORMATION FOR SEQ ID NO:7:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CGACGAGCGT GACACCACGA TGCCTG 26

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GGTGTCACGC TCGTCGTTTG GTATGGCTTC 30

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GAAGCCATAC CAAACGACGA GCGTGACACC 30

COMPOSITIONS AND METHODS FOR USE IN DETECTION OF ANALYTES

BACKGROUND OF THE INVENTION

The present invention relates generally to the biological and chemical arts. In particular, the present invention is directed to compositions and methods useful in qualitative and quantitative assays of compounds of interest in the chemical and biological arts.

A wide variety of techniques have been developed for determining the concentration of one or more compounds (generally referred to as analytes) in a liquid sample. In many of these methods, use is made of antibodies or fragments thereof which bind specifically to the analyte. In particular, antibodies bound to a solid support have been employed in a variety of sandwich-type and competitive assays.

While the use of antibodies or fragments thereof has the distinct advantage of the specificity of these reagents for the target analytes, there are nonetheless significant disadvantages with the heretofore-known assay systems. For example, when antibody is bound to a solid support, reaction between antibody and analyte can only occur in a heterogeneous immunochemical reaction; it is well known, however, that the kinetics of such reactions in a homogeneous solution phase are much more favorable. In addition, antibody bound to a solid support is often not reusable for a plurality of assays. Further, for each specific analyte it is necessary to provide a unique product comprising antibody bound to solid support. It would clearly be advantageous to provide assay systems wherein a solid support component could be used in a variety of different assays and could be reused without loss of effectiveness.

It is an object of the present invention to provide novel assay methods and compositions for use therein which do not suffer from the drawbacks of the prior art methods and compositions.

SUMMARY OF THE INVENTION

In accordance with the present invention, double stranded nucleic acid duplexes serve as universal, reusable, harvestable and clearable rink systems in a variety of different types of immunoassays (e.g., sandwich, competitive, etc.). Depending upon the type of assay, at least one specific component involved in the assay system is attached to a first member of a pair of sequences forming a double stranded nucleic acid (i.e., two oligonucleotides comprising substantially complementary sequences). Pursuant to the present invention, the assay is carried out in the presence of a support to which is attached an oligonucleotide which is the other member of the pair of sequences forming a double-stranded nucleic acid duplex under hybridization conditions. Upon the hybridization of the two complementary oligonucleotides to form a duplex, the component of the assay system to which the first member of the pair of oligonucleotides is attached may thereby be effectively removed from the solution phase and harvested onto the support. Oligonucleotides bound to a support are reusable in multiple successive assays. Moreover, any given support-bound oligonucleotide can be used in accordance with the present invention for the analysis of a variety of different analytes.

DETAILED DESCRIPTION OF THE INVENTION

Pursuant to one preferred aspect of the invention, the assay system comprises a sandwich assay. In preferred embodiments of sandwich assays in accordance with the present invention, a homogeneous immunoreaction wherein all of the components are in the solution phase is employed to form an immunochemical conjugate among an analyte and immunoreagents for the analyte. This format is in general less commonly used, but it is advantageous due to the highly favorable immunochemical reaction kinetics in the homogeneous phase. For purposes of the present invention, however, it is also contemplated that heterogeneous systems (i.e., systems in which complex formation occurs with a solid-phase component) may be employed in some cases. These heterogeneous systems are more commonly employed, but are somewhat less desirable in accordance with the present invention because of the slower kinetics and hence higher amounts of relatively expensive antibody required. The sandwich assay is highly sensitive, because there is no signal detected in the absence of analyte; therefore, it is particularly appropriate for use with analytes present in low concentrations (i.e., concentrations below about $10^{-8}M$). In addition, the sandwich assay is especially suitable for determining the concentration of large molecules (e.g., proteins).

In accordance with this embodiment of the invention, two immunoreagents which specifically bind to the analyte are employed in the sandwich assay. A first immunoreagent includes an oligonucleotide which is one member of the pair of sequences forming a double stranded nucleic acid. A second immunoreagent may include a suitable labeling agent, the concentration of which may be readily determined in a manner as generally known in the art.

Each of the immunoreagents also contains a suitable immunoreactant. For purposes of the present invention, an immunoreactant is defined as a protein (i.e., an amino acid sequence comprising more than 50 amino acids) or peptide (i.e., an amino acid sequence comprising 50 or less amino acids) which binds specifically to the analyte. Typically, the immunoreactant is a monoclonal or polyclonal antibody to the analyte or a portion thereof (e.g., an Fab' fragment) which specifically binds to the analyte. However, as would be appreciated by those working in the field, the formation of a specific conjugate comparable to the binding of an antibody to an antigen may be achieved through the use of other specific protein- or peptide-based binding systems (e.g., a receptor protein or fragment thereof and a ligand therefor) which would not generally be considered to involve immunochemical conjugate formation; nonetheless, such proteins or peptides are considered as within the scope of the class of immunoreactants suitable for use for purposes of the present invention. Further, analogues and variants of various immunoreactants (for example, those generated using recombinant DNA techniques) which specifically bind to the target analyte are contemplated as within the scope of the present invention.

Because it is necessary to form a conjugate of the analyte with both immunoreactants in a sandwich assay, it is generally appropriate to use immunoreactants which bind specifically to different epitopes of the analyte. Thus, two different monoclonal antibodies (or portions thereof) which bind non-competitively to the analyte (and thus, presumably bind to different sites on the analyte) are suitably employed in formation of the first and second immunoreactants. As is well known to those working in the field, suitable monoclonal antibodies to a variety of epitopes may be routinely generated in a manner known per se. Any two antibodies may then be routinely screened to confirm their suitability for use in accordance with the present invention.

The kinetics of a homogeneous reaction among the two immunoreagents in solution and the analyte to form a conjugate are usually significantly faster than would be the case with a reaction between solution-phase materials and a solid material (e.g., an immunoreagent bound to solid support). Accordingly, it is preferred in accordance with this aspect of the invention that the formation of the sandwich-type conjugate be carried out in solution prior to contacting any of the components of the assay system with the solid support. Nonetheless, it is contemplated as within the scope of the invention to combine all of the components of the assay system simultaneously or to combine any of the components with one or more other components in any order.

In accordance with preferred embodiments of the sandwich assay in which conjugate is formed among the two immunoreagents and the analyte in solution, the reaction mixture containing the conjugate and unbound material may then be contacted with the support to which is attached an oligonucleotide which is the other member of the pair of sequences forming a double-stranded nucleic acid duplex under hybridization conditions. Upon the hybridization of the two complementary oligonucleotides to form a duplex; the conjugate comprising one of the oligonucleotides is effectively harvested onto the support. Only labeled immunoreagent bound through conjugate formation is harvested onto the support by the process of duplex formation. Any labeled material not bound to the immunoconjugate remains in the solution phase and may readily be separated from the support and materials bound to the support.

The concentration of the label may be measured by any number of conventional procedures appropriate to the label employed to provide a measure of the concentration of the analyte. The double stranded nucleic acid forming the duplex used to harvest the complex may be appropriately denatured (for example, by the addition of water or low salt buffer) and the labelled conjugate released from the oligonucleotide attached to the support prior to measurement of the concentration of label. Alternatively, the concentration of label may be measured while the immunoconjugate remains bound to the support.

In alternative embodiments of the present invention, competitive assay systems are provided. As would again be readily appreciated by those working in the field, these competitive assays are particularly useful for detecting the presence of smaller analytes (e.g., organic molecules) or multiple analytes in a sample (e.g., drug analysis of a patient fluid sample). Sandwich assays of multiple analytes are also possible in accordance with the present invention. Pursuant to the competitive binding embodiments, only one immunoreactant is employed. As in the sandwich-assay embodiment, use is also made of complementary first and second oligonucleotides; in all assay systems, one of the oligonucleotide sequences is bound to a suitable support.

In one embodiment of competitive assay, the first oligonucleotide is bound to analyte or to an analog thereof which competes with the target analyte for the immunoreactant. The second oligonucleotide is bound to a support; in one preferred embodiment, the second oligonucleotide may be bound to a suitable sensor. Using drug analysis as an example, a different oligonucleotide may be bound to each of a group of drug molecule species (or analogs thereof) for which the concentration is to be determined. In this embodiment of a competitive assay, a suitable label (e.g., fluorescein) is bound to an immunoreactant (e.g., an antibody or receptor) for each of the drug molecules. After the competitive reaction of each of the drug molecules from the sample and its corresponding competitor (with oligonucleotide attached thereto) for the immunoreagent (comprising immunoreactant and label), each sensor harvests its complementary oligonucleotide by duplex formation as in the previous embodiment. Bound, labeled antibody is inhibited by an amount dependent on the concentration of that particular drug in the sample. The amount of competitive inhibition is then determined in a suitable manner (for example, by measurement at the appropriate sensor in those embodiments in which the support comprises a sensor), typically after washing residual solution from the sensor surface.

In an alternative embodiment of competitive assay, an immunoreagent is employed in the form of an immunoreactant which binds specifically to the analyte and which has a first oligonucleotide attached thereto. In this embodiment, a suitable label is attached to an analyte competitor. In its simplest form, the competitor may suitably comprise an analyte molecule to which the label is attached, either directly or through a suitable linker group. Alternatively, an analog of the analyte which binds competitively to the immunoreactant is attached to the label. Analyte and analyte competitor both compete for the immunoreactant, and the complexes formed by both analyte and analyte competitor with the immunoreagent are bound to the support by duplex formation between the first oligonucleotide (forming part of the immunoreagent) and the second oligonucleotide bound to the support. The concentration of analyte is then determined by measuring the reduction in binding of label to the support relative to the baseline value obtained in the absence of analyte. Alternatively, the amount of label remaining in solution may of course be determined.

In some instances, it is desired to separate various analytes from solution comprising same; after these analytes are separated from the solutions (including any potentially interfering components thereof), the amount thereof present in the solutions can be determined in a manner known per se without the use of label bound to some component of the assay system. For some analytes (e.g., hemoglobin and hemoglobin A1c), moreover, the inherent absorptivity of the specific protein can be used for quantitation. Thus, the difference between the absorbances of immunoreagent and immunoreagent and analyte would provide a direct measure of the analyte present. In addition, it is possible in some instances to pre-label all of the analytes in a sample; for example, proteins could be pre-labelled with Cy5 and each protein quantified by fluorescence measurement. Therefore, in accordance with some embodiments of the present invention pairs of complementary oligonucleotide sequences are employed to facilitate the harvesting of analytes of interest. In these embodiments, an immunoreagent for the analyte is employed comprising an immunoreactant which binds specifically to the analyte and a first oligonucleotide sequence attached thereto; a second oligonucleotide sequence complementary to the first oligonucleotide sequence is bound to a support. Immunochemical complexes formed between the immunoreactant and analyte are harvested as previously described by duplex formation between the first and second oligonucleotides. After removing the support from the solution and cleaving the duplex to release the immunocomplex, the analyte is effectively released into the solution. The quantity of analyte thus released may then be quantified in an appropriate manner (e.g., measurement of absorbance, fluorescence of label attached to analyte, etc.). As with the other embodiments heretofore discussed, this approach is suitable for use for quantification of multiple analytes. In some instances, separation of components (e.g., by chromatography or electrophoresis) may be necessary or appropriate before detection.

For use as oligonucleotides in all of the assay systems in accordance with the present invention, both homopolymer systems (i.e., Poly dA •Poly dT and Poly dG •Poly dC where dA, dT, dG and dC are deoxyadenosine, deoxythymidine, deoxyguanosine, and deoxycytidine, respectively) and heteropolymer systems have been shown to work quite efficiently. In particular, heteropolymers permit the detection of multiple analytes in a single sample through the use of specific pairs of sequences for harvesting and displacement of each analyte. Suitable oligonucleotides include, but are not limited to, those comprising conventional DNA and RNA bases, DNA/RNA base analogs [see, e.g., Frauendorf, A. & Engels, J. W., *Studies in Natural Products Chemistry* 13, 257 (1993); Milligan, J. et al., *J. Medicinal Chem.* 36, 1923 (1993)] and peptide nucleic acids [see, e.g., Hanvey, J. C. et al., *Science* 258, 1481 (1992); Burchardt, O. et al., *Trends in Biotechnology* 11, 384 (1993)]. In general, any oligonucleotides capable of base pairing (e.g., Watson-Crick duplex or Hoogstein triplex formation) would be suitable for use in accordance with the invention.

To ensure proper hybridization for harvesting, it is preferred that the oligonucleotides have a length of at least 6 bases, preferably about 10 bases, more preferably at least about 20 bases, and most preferably about 30 bases. As is well understood in the art, the strength of the duplexes formed is determined to some extent by the composition of the pair of oligonucleotides; in particular, stable duplexes may be formed with short (i.e., 6–10 base) oligomers using, e.g., modified bases or peptide nucleic acids.

In general, it is further preferred that the oligonucleotide pairs are completely complementary over at least a portion of their respective sequences. These complementary portions of the sequences should comprise at least 6 bases, preferably at least about 10 bases, more preferably at least about 20 bases, and most preferably at least about 30 bases. Of course, as is well understood in the art, using the appropriate low-stringency conditions it is possible to achieve hybridization even when there is a limited degree of mismatch between the two oligonucleotides. Nonetheless, for purposes of convenience the use of completely complementary sequences is preferred. In general, the amount of oligonucleotide bound to the support is in excess of the oligonucleotide in the other component of the assay system.

In accordance with one aspect of the present invention, novel oligonucleotide-antibody conjugates are provided in which an antibody or fragment thereof (in particular, a Fab' fragment) is linked to an oligonucleotide by a suitable linking agent. A variety of different coupling chemistries may be employed. Pursuant to one approach, a homobifunctional agent (for example, 1,4-phenylene diisothiocyanate) is employed. Pursuant to a presently preferred approach, a heterobifunctional reagent is employed; suitably, such a reagent includes a first reactive group (e.g., N-hydroxysuccinimide) specific for amino groups of the oligonucleotide and a second reactive group (e.g., maleimide) specific for thiol groups of the antibody or fragment thereof. The use of such heterobifunctional reagents provides substantially higher yields; whereas a homobifunctional agent may react with any of the multiple amino groups of an antibody or fragment thereof as well as the oligonucleotide (and thus, lead to a mixture of products), a suitable heterobifunctional reagent reacts specifically to form a one-to-one antibody/oligonucleotide conjugate.

As Fab' fragments have only one thiol group, they are particularly suitable for use in formation of conjugates with oligonucleotides. Moreover, Fab'-oligonucleotide conjugates often give superior results in immunoassays in accordance with the present invention relative to whole antibody-oligonucleotide conjugates, particularly in competitive binding assays. This may be rationalized by the fact that a Fab' fragment has only one binding region for the hapten or analyte, and hence provides greater sensitivity in the competitive binding reaction compared to the whole antibody (which has two binding regions for the hapten or analyte).

One presently preferred heterobifunctional agent for use in preparation of antibody/oligonucleotide conjugates is N-sulfosuccinimidyl 4-(N-maleimidomethyl)cyclohexane-1-carboxylate (Sulfo-SMCC). As would be readily appreciated by those skilled in the art, however, a variety of heretofore-known amino and sulfhydryl group directed cross-linkers could equally well be employed in accordance with the present invention. Such cross-linkers are described, for example, in Wong, S. S., *Chemistry of Protein Conjugation and Cross-linking*, CRC Press, Boca Raton, Fla. (1991), pp. 147–164, the entire disclosure of which is hereby incorporated by reference. Exemplary cross-linking agents of this type include the following: N-succinimidyl 3-(2-pyridyldithio)propionate; N-succinimidyl maleimidoacetate; N-succinimidyl 3-maleimidopropionate; N-succinimidyl 4-maleimidobutyrate; N-succinimidyl 6-maleimidocaproate; N-succinimidyl 4-(N-maleimidomethyl)cyclohexane-1-carboxylate; N-succinimidyl 4-(p-maleimidophenyl)butyrate; N-sulfosuccinimidyl 4-(p-maleimidophenyl)butyrate; N-succinimidyl o-maleimidobenzoate; N-succinimidyl m-maleimidobenzoate; N-sulfosuccinimidyl m-maleimidobenzoate; N-succinimidyl p-maleimidobenzoate; N-succinimidyl 4-maleimido-3-methoxybenzoate; N-succinimidyl 5-maleimido-2-methoxybenzoate; N-succinimidyl 3-maleimido-4-methoxybenzoate; N-succinimidyl 3-maleimido-4-(N,N-dimethyl)aminobenzoate; maleimidoethoxy[p-(N-succinimidylpropionate)phenoxy]ethane; N-succinimidyl4-[(N-iodoacetyl)amino]benzoate; N-succinimidyl 3-maleimido-4-(N,N-dimethyl)aminobenzoate; maleimidoethoxy[p-(N-succinimidylpropionate)-phenoxy]ethane; N-succinimidyl4-[(N-iodoacetyl)amino]benzoate; N-sulfosuccinimidyl 4-[(N-iodoacetyl)amino]benzoate; N-succinimidyliodoacetate; N-succinimidylbromoacetate; N-succinimidyl3-(2-bromo-3-oxobutane-1-sulfonyl) propionate; N-succinimidyl 3-(4-bromo-3-oxobutane-1-sulfonyl)propionate; N-succinimidyl 2,3-dibromopropionate; N-succinimidyl 4-[(N,N-bis(2-chloroethyl)amino]phenylbutyrate; p-nitrophenyl 3-(2-bromo-3-oxobutane-1-sulfonyl)propionate; p-nitrophenyl-3-(4-bromo-3-oxobutane-1-sulfonyl)propionate; p-nitrophenyl 6-maleimidocaproate; (2-nitro-4-sulfonic acid-phenyl)-6-maleimidocaproate; p-nitrophenyliodoacetate; p-nitrophenylbromoacetate; 2,4-dinitrophenyl-p-(β-nitrovinyl)benzoate; N-3-fluoro-4,6-dinitrophenyl)cystamine; methyl 3-(4-pyridyldithio) propionimidate HCl; ethyl iodoacetimidate HCl; ethyl bromoacetimidate HCl; ethyl chloroacetimidate HCl; N-(4-azidocarbonyl-3-hydroxyphenyl)maleimide; 4-maleimidobenzoylchloride; 2-chloro-4-maleimidobenzoyl chloride; 2-acetoxy-4-maleimidobenzoylchloride; 4-chloroacetylphenylmaleimide; 2-bromoethylmaleimide; N-[4-{(2,5-dihydro-2,5-dioxo-3-furanyl) methyl}thiophenyl]-2,5-dihydro-2,5-dioxo-1H-pyrrole-1-hexanamide; epichlorohydrin; 2-(p-nitrophenyl)allyl-4-nitro-3-carboxyphenylsulfide; 2-(p-nitrophenyl) allyltrimethylammonium iodide; α,α-bis[{(p-chlorophenyl) sulfonyl}methyl]acetophenone; α,α-bis[{(p-chlorophenyl)

sulfonyl}methyl]-p-chloroacetophenone; α,α-bis[{(p-chlorophenyl)sulfonyl}methyl]-4-nitroacetophenone; α,α-bis[(p-tolylsulfonyl)methyl]-4-nitroacetophenone; α,α-bis[{(p-chlorophenyl)sulfonyl}methyl]-m-nitroacetophenone; α,α-bis[(p-tolylsulfonyl)methyl]-m-nitroacetophenone; 4-[2,2-bis{(p-tolylsulfonyl)methyl}acetyl]benzoic acid; N-[4[2,2-2{(p-tolylsulfonyl)methyl}acetyl]benzoyl]-4-iodoaniline; α,α-bis[(p-tolylsulfonyl)methyl]p-aminoacetophenone; N-[{5-(dimethylamino)naphthyl}sulfonyl]α,α-bis[(p-tolylsulfonyl)methyl]-p-aminoacetophenone; and N-[4-{2,2-bis(p-tolylsulfonyl)methyl}acetyl]benzoyl-1-(p-aminobenzyl)diethylenetriaminepentaacetic acid.

Various aspects of the invention may be illustrated by a more detailed discussion of several exemplary assays. In one example of the sandwich assay, the use of antibodies (identified as $Ab_1$ and $Ab_2$) each of which binds to a particular epitope of the analyte (for example, TSH) is illustrated. One of these antibodies $Ab_1$ is suitably linked in a manner known per se to an oligonucleotide (for example, poly dT). The other antibody $Ab_2$ is similarly suitably linked to an appropriate labeling agent (for example, HRP) to be used in determining the concentration of the analyte to which the antibodies employed specifically bind.

In the sandwich assay, a complex is formed among the analyte, the immunoreactant attached to the oligonucleotide and the immunoreactant attached to the labeling agent. As would be apparent to those working in the field, the formation of the complex in solution for all types of assay may be effected under a wide range of conditions. The time required for formation of a sufficient concentration of complex in solution to enable efficient measurement is dependent to a great extent upon the concentrations of the analyte and immunoreactant(s); in general, complex formation would occur more rapidly for a given concentration of analyte at higher immunoreactant concentration. Therefore, it is preferred that there be an excess of immunoreactant, and most preferably at least a two-fold excess of immunoreactant, relative to analyte. The range of analyte concentrations which may conveniently be measured using the sandwich assay format is particularly broad; analytes present in concentrations of from about $10^{-1}M$ to about $10^{-22}M$ may be measured by a sandwich assay.

Formation of a suitable concentration of complexes using all of the various types of assays may occur as quickly as in a few seconds or require as long as 24 hours; preferably, the complex formation step requires less than about 6 hours, and most preferably less than about 3 hours. Complex formation may also occur over a wide range of temperatures, which is limited at the upper end by the denaturing temperature of the immunoreactant(s); preferably, the complex formation is carried out at a temperature in the range of about 15° C. to about 70° C., and most preferably (for purposes of convenience) at room temperature. The pH may also be varied over a fairly broad range, with the limiting factor again being denaturation of the immunoreactant; the pH is normally in the range of about 2 to about 11, preferably about 4 to about 10, and most preferably close to 7. As is well known in the art, the addition of various materials, such as horse or fetal calf serum proteins, may be useful to keep materials in solution and minimize non-specific interactions; such additives, however, are not critical. Complex formation is typically carried out in aqueous solution, optionally containing up to about 25% of a suitable non-aqueous component (e.g., alcohol, ether, glycol, etc.).

When the complex is brought into contact with the support for hybridization of the complementary oligonucleotides, the complex becomes reversibly bound to the support by formation of a duplex. The determination of optimum conditions for formation of a duplex between the complementary oligonucleotides employed in accordance with the present invention may be determined empirically in an essentially routine manner. In general, as is well known in the art, the presence of a salt (e.g., NaCl, KCl, $NH_4Cl$, quaternary ammonium salts, etc.) at a concentration of about 0.1M to about 3M is preferred to facilitate hybridization. Otherwise, the conditions described above for formation of the complex are equally suitable for duplex formation.

In particular, the temperature at which 50% duplex formation for a pair of complementary oligonucleotides (referred to as the melting temperature, or $T_m$) occurs may be routinely determined for any given pair of oligonucleotides. The $T_m$ is dependent upon a number of factors, including the length and composition of the sequences and the binding affinity of the particular bases employed in the oligonucleotides. For any given pair of complementary oligonucleotides, the $T_m$ may be routinely determined spectrophotometrically by varying the temperature and measuring the absorbance at a particular wavelength (e.g, 254 nm). Once the $T_m$ is determined for any pair of oligonucleotides, it is generally desirable to use a temperature below the $T_m$ so as to obtain greater than 50% binding. In general, duplex formation occurs at a temperature within the same range as complex formation; to increase the amount of duplex formation, lower temperatures are preferred.

The support and materials bound thereto may then be physically separated from the solution containing unbound materials. Any reagents which are non-specifically associated with the support but have not formed a complex may then be easily removed, for example, by gentle rinsing of the support. Use of appropriate conditions (e.g., a suitable salt concentration in the rinse solution) during the rinsing step is appropriate to ensure that any duplexes formed are not prematurely dissociated.

Finally, the bound complexes may be released from the support using appropriate denaturing conditions. The amount of label associated with the target compound is then measured by suitable means determined by the nature of the label (e.g., enzymatic label, colored label, fluorescent label, chemiluminescent label, etc.) before or after the bound complexes are released.

A wide variety of supports may be used in accordance with the present invention. For use in a variety of conventional assay methods, granular or pulverulent solid supports are particularly suitable. These materials typically have a particle size in the range of about 1 μm to about 1 inch. Suitable materials for preparation of this type of solid support include, but are not limited to, the following: polyvinylidene methacrylate (e.g., available commercially as Fractogel from Merck, Darmstadt, Germany and as Toyopearl from TosoHaas, Philadelphia, Pa.); polypropylene; polystyrene; glass beads; cellulosic materials, such as cellulosic filter paper (e.g., Actigel and Biobind as available commercially from Sterogene Bioseparation, Inc., Arcadia, Calif.); and polyvinylidene fluoride or PVDF (available commercially as Immobilon from Millipore, San Francisco, Calif.). The solid support may also be employed in a variety of forms, including but not limited to membranes and fibers; further, the support may be coated onto various materials (such as pipette tips, microtiter plate wells, test tubes, etc.). Presently preferred for use as supports are polyvinylidene methacrylate and polyvinylidene fluoride.

Exemplary polyvinylidene methacrylate products (e.g., the aforementioned Fractogel and Toyopearl products) are hydrophilic macroporous packings well known to those working in the field as suitable for use in bioprocessing chromatography. The products are methacrylate-based supports copolymerized with polyvinyl alcohol; their methacrylic backbone structure makes the spherical beads rigid. They are stable at pH 1 to 14 and at temperatures up to 100° C., resistant to chemical attack and not degraded by microbes. The packings are available in various pore size ranges; particularly suitable for use in accordance with the present invention are Toyopearl HW-75 and Fractogel-75F, which have a particle size of about 45 μm ["TosoHaas TSK-GEL Toyopearl," TomHaas, Philadelphia, Pa. (March 1989)]. Other suitable materials with comparable properties would of course be readily apparent to those skilled in the art.

An exemplary polyvinylidene fluoride material for use in accordance with the present invention is the aforementioned Immobilon AV Affinity Membrane. This product is a chemically activated, hydrophilic microporous membrane to which a variety of ligands can be covalently immobilized. The solid phase matrix offers a high capacity for covalent immobilization (>100 μg/cm$^2$) with retention of biological activity. The base membrane material is a non-interactive polymer (hydrophilic polyvinylidene difluoride) that has low levels of non-specific protein adsorption (<1 μg/cm$^2$). The entire external and internal surface of the membrane is chemically derivatized to allow for covalent immobilization of materials containing amino groups ["Immobilon AV Affinity Membrane," Millipore, San Francisco, Calif. (June 1988)]. Again, other comparable materials would be apparent to those working in the field.

Yet another suitable solid support material is optical fibers. Fiber optic chemical sensors bearing chemically selective immobilized reagents have the potential to be fast, sensitive and specific analytical tools. These sensors exploit the optical properties of interfaces between two transparent media having different refractive indices. Under appropriate conditions, fight can propagate within an optical waveguide (such as a quartz rod immersed in an aqueous solution) by total internal reflection. As part of this process, an evanescent wave penetrates a fraction of a wavelength into the aqueous phase and can optically interact with molecules located within a thin evanescent wave zone outside the waveguide surface. In particular, fluorescent molecules bound to the fiber surface may fall within this evanescent wave zone and may be excited by the evanescent wave. An oligonucleotide covalently bound to the optical fiber can be employed in accordance with the present invention to harvest immunochemical conjugate containing a fluorescent label. As a result of this process, the fluorescent labels (which are indicative of analyte concentration) are brought into the evanescent wave zone at the fiber surface and are excited by light propagating along the fiber axis. The resultant fluorescent emission is captured by the fiber and carried by total internal reflection to a detector located at the end of the fiber.

The unique advantage of applying the present invention to fiber optic detection is that the optical fiber can be regenerated by simple denaturation of the double stranded nucleic acid complex, thus making it ready for measurement of another analyte sample. By using different fluorescent molecules of distinctly different excitation and/or emission wavelengths, simultaneous multiple analyte measurements can be made. Alternatively, simultaneous measurements can also be made by coating different fibers or bundles of fibers with different oligonucleotides, each corresponding to a specific analyte. After harvesting the signals from the homogeneous phase, a particular set of fibers may be activated at a time and the fluorescence measured to determine the concentration of a particular analyte.

The oligonucleotides may be bound to the support using a variety of known techniques. Pursuant to one approach, the oligonucleotide is synthesized directly on the support in a manner as conventionally employed in the synthesis of oligonucleotides for other purposes; both particulate and membrane supports may be suitably employed as a substrate for oligonucleotide synthesis. Alternatively, an oligonucleotide containing a reactive functionality (e.g., an amino or thiol group) may be immobilized onto a support containing a suitable functionality reactive therewith, forming a covalent bond between the oligonucleotide and the support. Yet another approach involves attachment of the oligonucleotide to the support by affinity binding; for example, a biotinylated oligonucleotide may be immobilized onto a support containing avidin or streptavidin. Of course, as would be apparent to those working in the field other techniques may equally well be employed to attach the oligonucleotide to the support.

To dissociate the complementary oligonucleotide duplexes, a wide variety of methods may suitably be employed. Optimum conditions for any pair of oligonucleotides may conveniently be determined in a routine empirical manner. In many cases, deionized water may be used as the cleaving reagent; this is believed to lower the Tm of the hybrid due to the increased charge—charge repulsion present in a medium of low ionic strength, as compared to the one with a higher ionic strength present at the time of harvesting. In cases where the cleavage of the hybridized pairs is not as rapid or as quantitative as desired, a concentrated (e.g., 7M) urea or formamide solution (e.g., 30%-60% in water) may suitably be used for cleavage. This generally gives near quantitative release and also has the advantage that it facilitates successful reuse of the same support over many cycles; however, some enzyme labels may be sensitive to such treatment. Cleavage may also be made near quantitative using deionized water at elevated temperatures.

The detection method to be used is determined by the type of label. For modest sensitivity, a fluorescent label could be used. The fluor may be measured while bound to the solid phase in the chamber, or after release into a solution capable of cleaving the cleavable link. Measurement of the released label may in many cases be more precise and convenient than measurement of the bound label. A wide range of heretofore known fluorescent labels may be suitably employed in accordance with the present invention, including, but not limited to, the following: fluorescein, rhodamine and derivatives thereof, coumarin and derivatives thereof, hexamethylindotricarbocyanine and derivatives thereof, and diethylthiacarbocyanine and derivatives thereof. The label is appropriately attached to the immunoreactant forming the second immunoreagent (or, in some cases, to an analyte or competitive analog thereof) by a variety of heretofore known chemical methods, as are conventional for these labels and would be readily apparent to those skilled in the art; suitable techniques are described, for example, in Wong, supra.

Pursuant to one embodiment the solid phase may comprise an optical fiber and the label a fluorescent molecule. Measurement of concentration of the label may suitably be effected by fiber optic detection using evanescent wave biosensor technology, after which the immunoconjugate can be removed from the support to prepare the support for reuse. The ability to employ a single biosensor in multiple successive assays is a significant advantage relative to prior an techniques. A similar approach may be employed with other types of labels (for example, enzymatic labels).

For more sensitive tests enzyme labels are frequently employed, because the amplification of the signal through the enzymatic reaction provides a more intense and more easily measurable response. Enzyme labels, however, typically require incubation (often for a considerable period of time) of a substrate solution with the bound enzyme in a suitable reaction vessel, such as the reaction chamber of an automated system or after release from the chamber upon cleaving the duplex. Exemplary enzyme labels which are well known for use include the following: alkaline phosphatase, horseradish peroxidase, β-galactosidase, etc.

Because of their high sensitivity, rapid response, and tendency to be destroyed by the process of measurement, chemiluminescent labels are particularly suitable for use in a clinical autochemistry system. Such chemiluminescent labels are described in, e.g., Campbell, A. K., *Chemiluminescence: Principles and Applications in Biology and Medicine*, Ellis Horwood, England (1988), hereby incorporated by reference. Labels well-known in the art as suitable for this purpose include, but are not limited to: acridinium esters, luminol and its derivatives, dioxetane derivatives, aequorin and luciferins. With some of these labels (e.g., acridinium esters), a suitable trigger reagent (e.g., alcoholic hydrogen peroxide for acridinium ester labels) may be added to release the light while the label is bound to the solid phase within the chamber. Alternatively, the complex containing the label may first be released from the duplex and then reacted in solution with a trigger reagent in a separate measuring chamber. Following the light release reaction, most labels of this type are unable to provide a subsequent signal; this minimizes the danger of carryover of label upon re-use of the solid support.

The overall procedure for a sandwich assay is generally illustrated (for the exemplary analyte TSH, thyroid stimulating hormone, and the label HRP, horseradish peroxidase) as follows in Scheme I:

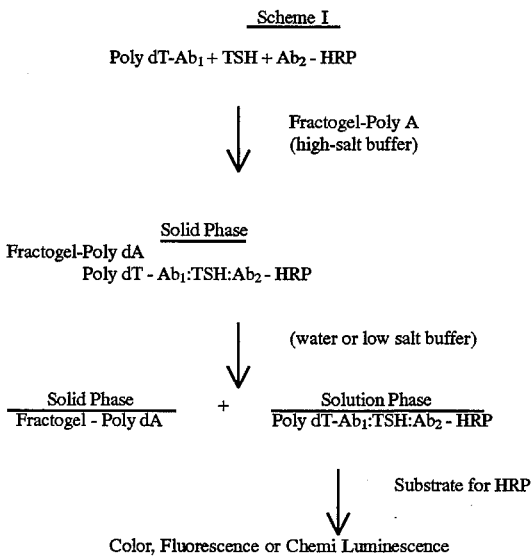

Pursuant to one preferred embodiment of the invention, a strand displacement method is employed to cleave the duplexes formed upon harvesting of the immunochemical complexes. In this approach, an oligonucleotide hybrid is dissociated by competitive binding of one member of the hybrid pair to an excess of its complement. This makes it possible to use a mixture of solid supports simultaneously, each solid support having a different oligonucleotide bound thereto to harvest label-bearing immunochemical reaction complexes comprising complementary oligonucleotides. Release of each label-bearing immunochemical reaction complex may then be effected sequentially to permit selective measurement of associated label. In a first approach, strand displacement is effected using an oligonucleotide sequence corresponding essentially to that of the first oligonucleotide (i.e., the oligonucleotide bound to the first immunoreactant to form the first immunoreagent). Pursuant to this approach, the displacement agent is used in excess to compete with the first immunoreagent in binding to the support. For example, dT25-HRP (dT25 is 25 deoxythymidine units) and Fractogel-dA30 (dA30 is 30 deoxyadenosine units) were used as a binding pair and dT25-HRP released from the Fractogel-dA30 by competitive displacement using dT25. Displacement was observed upon addition of a substantial excess of dT25.

In an alternative approach, as strand displacement agent an oligonucleotide sequence corresponding essentially to the second oligonucleotide (i.e., the oligonucleotide bound to the support) is employed. In the above example, this would entail use of dA-oligonucleotide (e.g., dA30) as the releasing agent. This approach offers several significant advantages. First, it is generally easier for a displacement agent corresponding to the first oligonucleotide to bind to any open site on the support than to displace an already bound sequence corresponding to the first oligonucleotide. Moreover, any conjugate comprising the first oligonucleotide displaced by a displacement agent corresponding to the first oligonucleotide may subsequently become bound to remaining available sites on the support; thus, it is particularly advantageous to block all the available sites on the support with oligonucleotide corresponding in sequence to the first oligonucleotide before the immunochemical conjugate is displaced. Displacement agent corresponding to the second oligonucleotide cannot bind to the support, but only through displacement of the immunochemical complex. Therefore, a displacement agent corresponding to the second oligonucleotide may be more effective than the bound second oligonucleotide in competing for the immunochemical conjugate. Finally, displacement by an agent corresponding to the second oligonucleotide sequence leaves the solid support ready for reuse, whereas after displacement by a sequence corresponding to the first oligonucleotide sequence, the support would need regeneration by denaturing the resultant displacement agent/support duplexes. This is a particular advantage in performing sequential immunoassays on automated clinical chemistry systems.

This approach is delineated below in Scheme II:

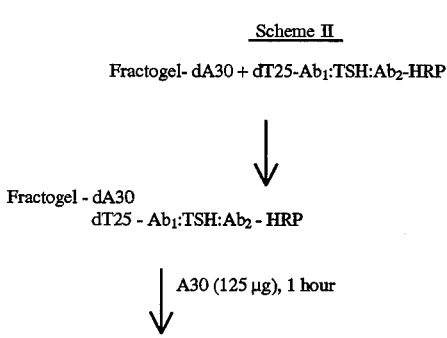

-continued
Scheme II

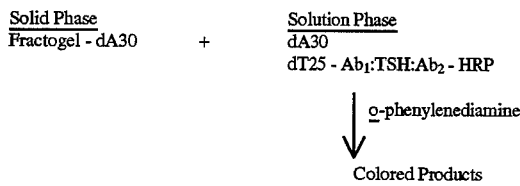

In a further experiment, a system based on phenobarbital was employed to demonstrate the method of the present invention with another analyte in a competitive assay mode.

Accordingly, a phenobarbital antibody Fab'-dC20 conjugate and Fractogel-dG25 were prepared. The assay was performed as delineated below in Scheme III, where Pb is phenobarbital, Pb-F is a phenobarbital-fluorescein conjugate.

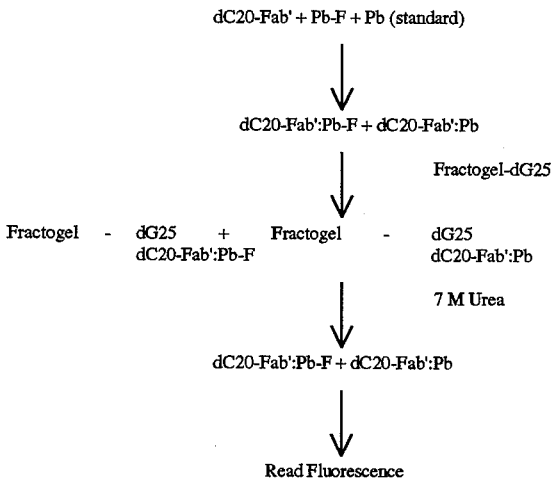

The system was initially standardized using 7M urea for releasing the signal and an acceptable standard curve was obtained. Subsequently, an acceptable standard curve was also obtained using a strand displacement method; this method worked effectively for both TSH and phenobarbital systems (giving about 20% release in one minute and 50% in 12 minutes).

Although the methods heretofore described are clearly advantageous in many instances, in some cases the cleavage process may be slower than is desired. Accordingly, pursuant to a further embodiment of this aspect of the invention the oligonucleotides can further be designed to enhance the release process. In accordance with this embodiment, heteropolymeric oligonucleotides are preferably employed, with the region of complementarity of the displacer to the reagent-carrying oligonucleotide to be displaced being sufficiently greater than the region of complementarity of the reagent-carrying oligonucleotide to the oligonucleotide on the solid support as to make the duplex comprising the displacer more stable. In general, the degree of overlap between the displacer and the reagent-carrying oligonucleotide should be greater by at least three bases, more preferably at least about five bases, and most preferably at least about eight bases than the overlap between the support-bound and reagent-carrying oligonucleotide.

One exemplary embodiment is illustrated below. The oligonucleotide 5' CAAAATACGTGGCCTTATGGTTA-CAG 3' (SEQ ID NO: 1) is bound to the Fractogel solid support. The oligonucleotide 5' AAGGCCACGTATTTTG-CAAGCTATTTAACT 3' (SEQ ID NO:2) is bound to the immunoreactant. The oligonucleotide 5' AGTTAAAT-AGCTTGCAAAATACGTGGCCTT 3' (SEQ ID NO:3) is employed as a displacer. L represents the detection label and I the immunochemical conjugate:

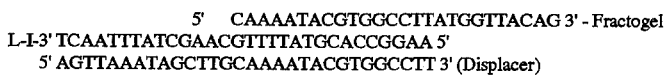

This system gave markedly accelerated kinetics, with nearly complete release in 10 minutes and about 80% release in one minute. As expected, the use of higher temperature further improved the rate of release, in the order 37° C.>30° C.>22° C. Whereas release in the comparable homopolymer system required 125 µg of displacer oligonucleotide, the enhanced system showed no significant difference between 2.5 µg and 125 µg of the displacer. It was also found that incorporation of a single base mismatch in the support-bound oligonucleotide did not affect the harvesting, but accelerated the release.

The enhanced displacement method was adapted to the phenobarbital assay. Displacement for one minute gave a very satisfactory standard curve over the range of 0 to 80 µg/ml of phenobarbital. There was no significant difference between the use of 2.5 µg and 125 µg of the displacer oligonucleotide. By optimizing the conditions, an acceptable standard curve with 1 minute homogeneous incubation, one minute harvesting and 1 minute displacement was obtained. It was demonstrated that the solid support could be used at least 8 times without a significant change in the signal.

In accordance with a particularly preferred aspect of the present invention, two or more analytes are measured simultaneously using one or more of the above approaches. The enhanced strand displacement method is particularly applicable to simultaneous multiple analyte measurement. In accordance with this particularly preferred embodiment, signals corresponding to each of the analytes can be selectively released by sequential elution with the appropriate complementary oligonucleotides. After release, the solid support is easily prepared for reuse. The multiple analyte capability can advantageously be utilized for performing analysis of multiple analytes from a single sample, following a single homogeneous immunochemical reaction involving multiple reaction partners.

A model system was defined for simultaneous measurement of two analytes, theophylline and phenobarbital. Each analyte was conjugated to fluorescein label. A theophylline monoclonal antibody was conjugated to a first oligonucleotide (Oligo-1) and a phenobarbital monoclonal antibody was conjugated to a second oligonucleotide (Oligo-2). A solid phase specific for the theophylline assay was prepared by synthesizing an oligonucleotide complementary to Oligo-1 (Oligo-1') on a Fractogel solid support. A solid phase specific for the assay of phenobarbital was prepared by synthesizing an oligonucleotide complementary to Oligo-2 (Oligo-2') on a Fractogel solid support. The two solid supports were then combined before the assay. Suitable displacement oligonucleotides (Oligo-1" and Oligo-2", respectively) were also prepared.

A sample containing the two analytes was subjected to a simultaneous homogeneous immunoreaction with the two analyte fluorescein conjugates and the two antibody-oligonucleotide conjugates. The immunoreaction mixture was next harvested on the combined solid phases. After washing the combined solid phases, the displacing oligonucleotides were sequentially added interspersed by washes. The fluorescence of the resulting solution phases were then measured. The readings provide an inverse measure of the analyte concentration in the sample. The two solid phase reagents may then be prepared for reuse, if desired, by washing with 7M urea followed by a buffer wash.

This multiple analyte system is illustrated in Scheme IV where Th is theophylline, Pb is phenobarbital, and F is fluorescein.

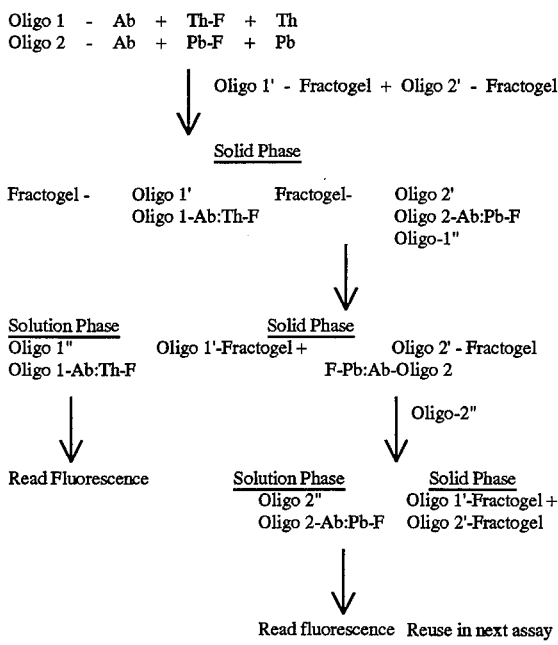

Of course, the concentration of each analyte may appropriately be determined sequentially following release of the corresponding complex from the solid support. In addition, the solid support is ready for reuse after completion of the assay. In a particularly preferred embodiment, enhanced displacement oligonucleotides as hereinbefore defined may be employed to facilitate sequential release of the harvested complexes. Using this approach, acceptable standard curves were obtained for both theophylline and phenobarbital, with both present in a single sample and measurements made sequentially following simultaneous immunoreaction.

The simultaneous measurement of three analytes (phenobarbital, theophylline and TSH) has also been carried out and acceptable standard curves for all of the three analytes obtained. In this model, phenobarbital and theophylline assays are competitive binding assays using fluorescein as a label, whereas TSH assay is a sandwich assay using HRP as a label. This demonstrates that assays of various different formats using different labels are compatible with the simultaneous analyte detection concept.

As would be readily apparent to a person skilled in the art, the assay formats described herein for purposes of illustration are by no means exclusive, nor are they necessarily alternatives. A wide range of different assay formats may be employed in a variety of procedures for measurement of analyte concentrations. In addition to conventional manual measurement procedures, assays in accordance with the present invention may be carried out using automated systems, for example with an accessory to a mainframe clinical analyzer.

In a dipstick assay format, a dipstick in the form of sheet or piece of plastic of suitable dimensions is provided with an attached oligonucleotide for use in harvesting an immunochemical conjugate comprising a complementary oligonucleotide and a label. The label can then be released, for example, by displacement using an appropriate oligonucleotide or by cleavage of the oligonucleotide link with a urea solution. Alternatively, microtiter plates with multiple wells or membranes with multiple distinct areas can serve as harvesting devices; analytes may be detected by a variety of means, such as fluorescence, chemiluminescence, electrochemiluminescence, a charge coupled device (CCD) camera arrangement, etc.

Multiple analytes in a single sample can similarly be determined in a number of different ways. Pursuant to one approach, multiple dipsticks (each with an attached specific oligonucleotide) are used to selectively harvest the appropriate immunoreaction complex. Each dipstick is then washed and inserted into a solution to release the labeled analyte. If desired, the signal may be read also on the dipstick. Alternatively, multiple oligonucleotides are located on a single dipstick. The individual analytes are selectively released by displacement with the appropriate oligonucleotide.

In a biosensor format, the biosensor surface (which may be a membrane or the front face of the sensing device itself) has bound thereto the second oligonucleotide. A biospecific reagent, conjugated to the complementary first oligonucleotide, is then suitably combined with the sample and a labeled reagent in a suitable reaction vessel (for example, a microtiter well) or in a flow system. After a brief period of homogeneous reaction (which generally proceeds rapidly), the sensor is put into contact with the sample in the reaction vessel or the flow stream is brought into contact with the sensor. After a brief contact time for harvesting, the sensor is removed from the first reaction vessel and immersed in a second reaction vessel containing wash solution with sufficient ionic strength to preserve the oligonucleotide hybrid binding. Similarly, in a flow system embodiment the wash solution is allowed to flow over the sensor surface. If the detection signal is a fluorescent label, it may be possible to make the measurement without even requiring a wash step; alternatively, the reading can be made directly after the wash step. If a chemical reaction is required to provide a detectable signal, the sensor may then be exposed to additional reagent(s) required and the signal then read. After the reading has been made, the sensor surface is suitably treated to dissociate hybrids formed (e.g., washing with a displacement agent and/or dissociation solution, followed by deionized water or other wash solution) to prepare it for the next measurement. The same sensing device may then be used for performing different tests, as a removable biospecific reagent is supplied for each desired test.

The use of a coating on or in close proximity to the sensing device has the advantage of providing greater sensitivity. In fluorescence or chemiluminescence measurements in particular, the advantage of close coupling of the signal source to the detector is substantial. With other modes of sensing, observation of a local reaction (rather than one occurring in bulk solution) may also provide enhanced sensitivity.

As would be readily apparent to those working in the field, this particular approach readily lends itself to many different implementations. In particular, the biospecific reagent is not necessarily integral to the sensor, and thus some embodiments do not precisely fit within a general definition of a biosensor. The re-usable harvesting member may be employed, for example, in the form of a coating on the inside of a measuring cell or cuvet. Reagents are pumped into or through the cell or cuvet, and the sensing device takes readings in or through the cuvet or in the solution pumped out of the cuvet. An automated clinical chemistry apparatus, equipped with a set of specially coated cuvets or microtiter plates with coated wells, could thus be employed advantageously to perform heterogeneous immunoassays in this manner. For this purpose, the cuvets are appropriately serviced during the reaction cycle.

In a particularly preferred embodiment, multiple determinations are performed on a single sample by employing a group of fluorescence sensors aligned along a flow channel or inserted through the side of a reaction vessel. Each sensor contacts the solution through a membrane which has an oligonucleotide bound to the side thereof facing the solution phase. Each membrane may contain a different oligonucleotide. Each of the biospecific reagents (e.g., antibodies or competitive-binding haptens) to be used is coupled to a different oligonucleotide complementary to one of the oligonucleotides bound to one of the membranes. A set of labeled biospecific reagents, each bound to the same fluorescent label (e.g., fluorescein), is also provided. The sample is allowed to react in a homogeneous solution reaction with the oligonucleotide-bound biospecific reagents and the labeled biospecific reagents. When the immunochemical complexes have been formed and the reaction solution brought into contact with the sensors, each different biospecific reagent (carrying its appropriate amount of bound labeled species) binds to the membrane on the surface of the corresponding sensor. A signal is then obtained at each sensor, the signal providing a measure of the concentration of a specific analyte. For use in this embodiment, sensors in the form of fiber optic probes capable of sensing fluorescence as evanescent waves are particularly useful.

In a heteroprocessor format, one or a combination of solid supports is contained in a suitable probe (e.g., within a disposable pipet or syringe tip). A particular advantage in accordance with the present invention is that such probes would be reusable; most prior applications of such probes have been limited to a single use. (An example of a single-use coated pipette tip is the one used by VIDAS Immunoanalysis System from bioMeriux Vitek, Inc., St. Louis, USA.) The homogeneous immunochemical reaction may be carried out, for example, in a well of a microtiter plate. The solution from the well is repeatedly contacted with the support in the tip for harvesting by successively aspirating and discharging the solution. After sufficient time for completion of harvesting, wash solution is similarly aspirated and discharged. The immunochemical complex reaction chain for a given analyte is then released by a suitable procedure (e.g., a displacement agent) using successive aspiration and discharge of the appropriate oligonucleotide. Multiple analytes are thus harvested from the same probe, each being released by contact with its corresponding displacement oligonucleotide.

In a flow-through system, solid support containing harvesting oligonucleotides is located within a tube. Sample containing analyte is moved through the tube, followed by sequential washes and displacements. The passage of solution through the tube is suitably accomplished using, e.g., a peristaltic or other pump to withdraw air from the collection tube; alternatively, air pressure may be used to push the fluids through the tube. A manifold of tubes may advantageously be used with a valving arrangement, or successive tubes may be attached to collect fractions. Alternatively, a set of tubes are provided in a turntable contained in an evacuable chamber; a peristaltic (or other) pump is employed to pull the liquid into the appropriate tube by evacuation. Movement of liquid through the tube can be accomplished using a peristaltic or other pump to force air into the source tube. A manifold of source tubes may be employed with a valving arrangement, or successive source tubes could be attached sequentially. Alternatively, a set of source tubes could be arranged for example in a turntable, contained in a pressurizable chamber, which could be pressurized to force the liquid from the appropriate tube into the exit line containing the solid support.

The invention may be better understood with reference to the accompanying examples, which are intended for purposes of illustration only and should not be construed as in any sense limiting the scope of the present invention as defined by the claims appended hereto.

EXAMPLE 1

Preparation of Fab'-oligonucleotide

For purification of antibody from ascites fluid using a Protein A affinity column, a Protein A column was equilibrated with 10 column volumes of binding buffer. The Protein A support, binding buffer (Catalog No. 21007) and eluting buffer (Catalog No. 21009) were obtained from Pierce, Rockford, Ill. The amount of ascites fluid that can be loaded (6 mg of antibody per 1 ml of gel) was calculated and then diluted 1:1 with binding buffer. The sample was loaded and run with 10 column volumes binding buffer. The column was eluted with eluting buffer (5 column volumes). The eluent was dialyzed with 0.1M sodium citrate pH=3.5 (4 changes).

Pepsin digestion of antibody to make $(Fab')_2$ was effected by dissolving 1 mg of pepsin in 100 μl of 0.1M sodium citrate pH=3.5 to which was added 25 mg of IgG sample. The sample was incubated for 4 hours at 37° C. The pH was adjusted to 7 with 3M tris(hydroxymethyl)aminomethane. An equal volume of saturated $(NH_4)_2SO_4$ was used to precipitate $(Fab')_2$. The sample was rocked overnight at 4° C.; thereafter, the material was centrifuged at 10,000 RPM for 60 minutes at 4° C. The material was redissolved in 3 ml of 0.1M $NaHCO_3$ pH=8.2 and dialyzed with 0.1M $NaHCO_3$ (4 changes).

To 3 ml of $(Fab')_2$ (about 8 mg or 11 $Abs_{280}$) was added 760 μl of 0.5M dithioerythritol (DTE) and 40 μl 0.5M EDTA; DTE was added dropwise. The solution was incubated at room temperature for 1 hour. The sample was loaded onto a 1.5×30 cm G25 column and Fab' was eluted with 0.1M PBS (1×) containing 5 mM EDTA (pH 7.0).

To prepare the 5' $NH_2$-derivative of the oligonucleotide (Oligo-$NH_2$) of the sequence 5' AAGGCCACGTATTTTG-CAAGCTATTTAACT 3' (SEQ ID NO:2) for binding with antibody or fragments thereof, 60 $Abs_{260}$ of oligonucleotide was dissolved in 500 μl of water. 7 mg of sulfosuccinimidyl 4-(N-maleimidomethyl) cyclohexane-1-carboxylate (Sulfo-SMCC; available commercially from Pierce) was dissolved in 500 μl of 0.2M $NaHCO_3$ pH=8.2. After mixing, the solution was incubated for 1 hour at room temperature. The sample was loaded onto a $G_{25}$ column (1.5×50 cm). SMCC-oligonucleotide was eluted with water.

To prepare Fab'-oligo conjugate, 2.78 g NaCl was added to 82.5 $Abs_{260}$ SMCC-oligo (~10 ml) and then 1000 μl of 10×PBS was added; 10×PBS was prepared by dissolving 80 g NaCl, 22 g KCl, 14.4 g $Na_2HPO_4$ and 2.49 g $KH_2PO_4$ in 1 liter of water (pH=7.4). The solution is vortexed to dissolve NaCl and then mixed with 6.6 mg of Fab'. Final concentrations were 3M NaCl and 2 mM EDTA. 2 ml aliquots are introduced into Centricon-3 filters (for a total of 8 Centricons) obtained from Amicon, Inc., Beverly, Mass. The samples were centrifuged at 6000 RPM and 23° C. for 2 hours. The samples were centrifuged for 3 more hours at 6000 RPM at 12° C. and then left in the centrifuge overnight. All tubes were combined, the Centricon-3 filters washed with 100 µl 0.1M Tris pH=8.05 mM EDTA and the washes combined. The product was then purified using a P100 Biogel 15×50 cm column from BioRad, Hercules, Calif. The column was eluted with water and the eluent fractions that contained 260 nm/280 nm absorbance ratios of about 1.25 were combined. The product was further purified on a DEAE Biogel 1.5×10 cm column from BioRad and eluted with a step gradient of 0.1M Tris/NaCl (i.e., 0.1M NaCl, 0.25M NaCl, 0.5M NaCl and 1M NaCl, all containing 5 mM EDTA pH 8.6). The ratio of $Abs_{260}/Abs_{280}$ of the conjugate usually was 1.5–1.7. The yield of isolated product was 85%.

in 100 µl of 0.1M sodium borate pH 9.3. The two solutions were mixed well and incubated in the dark at room temperature for 2 hours. The reaction mixture was extracted with 6 ml n-butanol/water (1:1) and the organic layer removed. An equal volume of n-butanol was added and extraction continued until the volume was about 100 µl. The combined extracts were dried by speed vacuum to provide the product (DITC-Oligo).

The DITC-Oligonucleotide was redissolved in 200 µl of 0.1M sodium borate pH 9.3 (total 73 $Abs_{260}$). 389 µl concentrated Pb-IgG (IgG antibody to phenobarbital) were added, the solution mixed well and incubated in the dark at room temperature overnight. The product was purified on a P100 column, eluted with 0.1M Tris(hydroxymethyl) aminomethane (pH 7.5), 5 mM EDTA. The fractions in the second peak were combined. The product was then purified with a DEAE Biogel A column equilibrated with 0.05M Tris

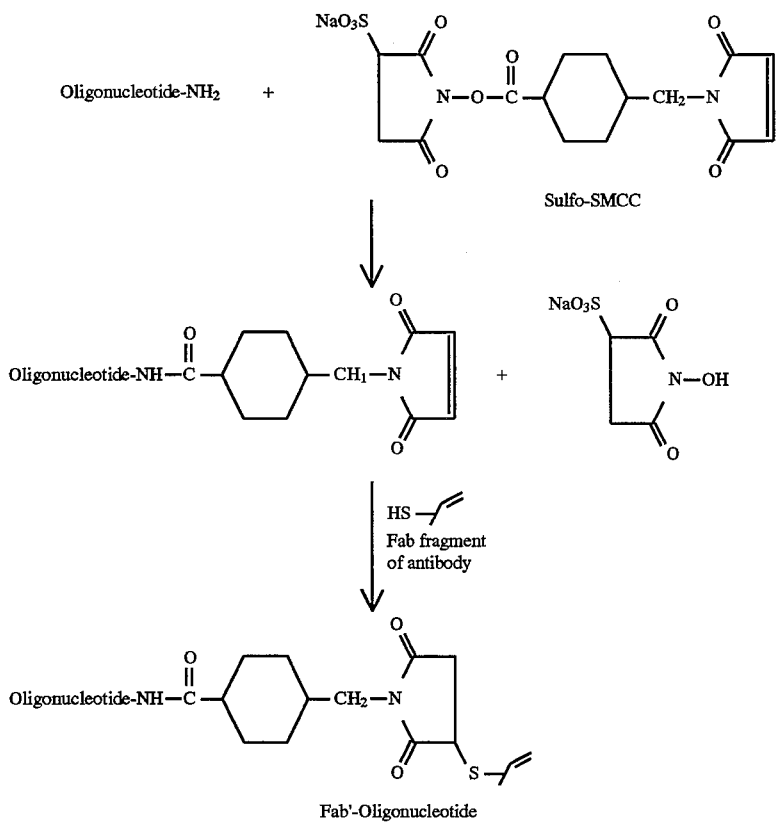

To check the quality of the Fab'-oligo conjugate, some of the Fab'-oligo conjugate was concentrated to 5 $Abs_{280}$/ml. An SPE-II Paragon Gel Kit (agarose gel) for electrophoresis obtained from Beckman Instruments was then employed in accordance with the manufacturer's instructions and the product stained with Coomassie Blue. The gel confirmed the formation of Fab'-oligonucleotide conjugate.

EXAMPLE 2

Preparation of Antibody-Oligonucleotide Conjugate Using DITC Linker

Antibody was purified from ascites fluid using Protein A in the manner described in Example 1. To prepare oligonucleotide for reaction therewith, 3.8 mg of 1,4-phenylene diisothiocyanate (DITC) was dissolved in 1.5 ml dimethyl formamide (DMF). 71 $Abs_{260}$ of Oligo-$NH_2$ was dissolved pH 8.6 and eluted with a step gradient of NaCl, 0.1M Tris pH 8.6, 5 mM EDTA as in Example 1. The fractions that were eluted with 0.25M NaCl were combined. The quality of the product Pb-IgG-Oligonucleotide (antibody to phenobarbital conjugated to oligonucleotide) was confirmed by running a Paragon SPE-II gel obtained from Beckman Instruments. The gels confirmed the preparation of the desired conjugate in about 30% yield.

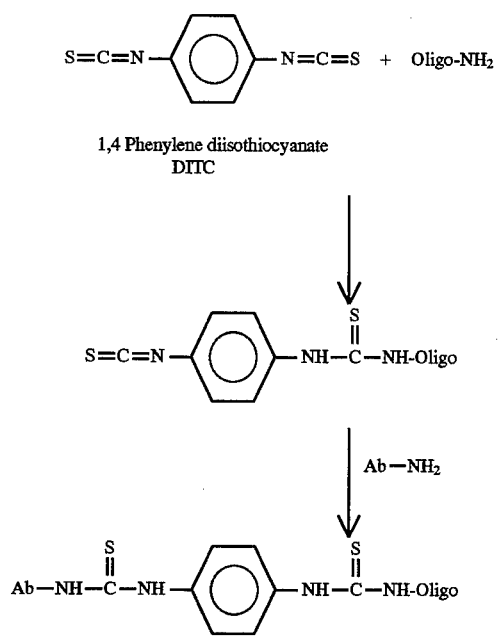

1,4 Phenylene diisothiocyanate
DITC

EXAMPLE 3

Preparation of Fractogel-Oligonucleotide

Fractogel-OH (150 mg) was packed in a 15 μmole column obtained from Millipore (South San Francisco, Calif.). Oligonucleotide was synthesized using the standard phosphoramidite chemistry [Gait, M. J., *Oligonucleotide synthesis: A practical approach*, IRL Press, Oxford, U.K. (1984)]. The solid support was introduced into a vial, 6 ml of concentrated ammonia added, the vial sealed and then heated for 4 hours at 65° C. The supernatant was decanted and the support washed with 20 ml of water. The process was repeated until the reading at 260 nm of wash solution was close to 0.0. This step ensured the removal of the protecting groups from the nucleosides.

EXAMPLE 4

TSH Immunoassay using Cellulose PolyA as Solid Support

In this assay, 200 μl of TSH standard (0, 0.1, 0.5, 2.5, 10, 25 and 50 μIU/ml) was mixed with 100 μl HRP-Ab$_2$ and 20 μl Poly dT-Ab$_1$ in a MCS membrane capsule of the type disclosed in U.S. Pat. No. 4,871,683 to Harris et al., the entire disclosure of which is hereby incorporated by reference. The mixture was incubated for 1 hour at 37° C. with shaking. 60 μl of cellulose-Poly dA slurry was added and the immunochemical conjugate harvested for 1 hour at 37° C. with shaking. The product was washed three times with 1 M NaCl. Orthophenylenediamine (OPD) reagent for the HRP was added and the mixture incubated 30 minutes at room temperature. The color was read at 492 nm. The results are reported in Table 1.

TABLE 1

| TSH std μIU/ml | 0 | 0.1 | 0.5 | 2.5 | 10 | 25 | 50 |
|---|---|---|---|---|---|---|---|
| Abs 492 nm | 0.052 | 0.055 | 0.096 | 0.393 | 1.257 | 2.828 | 4.545 |

EXAMPLE 5

TSH Chemiluminescence Immunoassay using Cellulose PolyA as Solid Support

200 μl of TSH standard (same as in Example 4) was added to 100 μl HRP-Ab$_2$ and 20 μl Poly dT-Ab$_1$ in a MCS capsule. The mixture was incubated for 1 hour at 37° C. with shaking. 60 μl of cellulose-Poly dA slurry was added and the immunochemical conjugate was harvested for 1 hour at 37° C. with shaking. The product was washed three times with 1M NaCl, 200 μl of water added to each capsule and the capsules heated for 10 minutes at 40° C. The supernatant was then transferred to glass tubes. 400 μl of Amerlite enhanced chemiluminescence signal reagent (Arlington Heights, Ill.) was added to each glass tube and light intensity measured after one minute on a Berthold Luminometer obtainable from Berthold Analytical Instruments, Gaithersburg, Md. The results are reported in Table 2.

TABLE 2

| TSH std μIU/ml | 0 | 0.1 | 0.5 | 2.5 | 10 | 25 | 50 |
|---|---|---|---|---|---|---|---|
| Light Intensity RLU | 2,527 | 4,553 | 20,993 | 108,005 | 585,141 | 986,133 | 1,100,991 |

EXAMPLE 6

TSH Sandwich Immunoassay using Enhanced Strand Displacement Method

In this assay, oligonucleotides having the following sequences were employed:

5' CATCGCCAGTCAGTATTCTCGGAGCA 3'     (SEQ ID NO:4)
5' ATACTGACTGGCGATGCTGTCGAAGTAGCG 5' (SEQ ID NO:5)
5' CGCTACTTCGACAGCATCGCCAGTCAGTAT 3' (SEQ ID NO:6).

As indicated, the oligonucleotides were attached to the solid support (SS) or antibody (Ab$_1$), or used directly as displacement agent:

```
                              5' CATCGCCAGTCAGTATTCTCGGAGCA 3'-SS
HRP-Ab2:TSH:Ab1-3' GCGATGAAGCTGTCGTAGCGGTCAGTCATA 5'
                 5' CGCTACTTCGACAGCATCGCCAGTCAGTAT 3' (Displacer)
```

In a series of capsules, TSH-standards (0, 0.25, 1, 5, 15 and 50 μIU/ml:200 μl) were added to TSH-Ab$_2$-HRP (100 μl)+ TSH-Ab$_1$-oligonucleotide (0.01 Abs$_{280}$). The mixtures were incubated at 37° C. for 30 minutes with continuous shaking. To each capsule was added 5 μl packed volume of Fractogel-oligonucleotide (TSH sequence SEQ ID NO:4) and the capsules shaken for 15 minutes at 37° C. All liquid was then blown out of the capsule and the solid support washed 3 times with 1M NaCl (which is also blown out). The TSH-displacer strand (1 Abs$_{260}$:200 μl in 1M NaCl) was added and the capsule shaken for 2 minutes at 37° C. The contents was blown out into a test tube, 100 μl pipetted out for color development (using OPD as substrate) and the absorbance measured. The solids were washed 2 times with 1M NaCl (which was then blown out).

To prepare the solid support for reuse, 200 µl of 7M urea was added to each capsule, the capsule shaken for 15 minutes at 37° C. and the contents blown out. The solid support was then washed 6 times with 1M NaCl to prepare the solid support for another assay.

The results are reported in Table 3.

TABLE 3

| TSH std µIU/ml | 0 | .25 | 1 | 5 | 15 | 50 |
|---|---|---|---|---|---|---|
| Abs at 492 nm | .054 | .087 | .147 | .268 | .715 | 2.174 |

EXAMPLE 7

Synthesis of Phenobarbital-F 58.92 mg (0.137 mmole) of amino-phenobarbital was dissolved in 2 ml of absolute ethanol containing 20 µl of triethylamine. 65.50 mg (0.126 mmole) of fluorescein isothiocyanate (isomer I, available from Aldrich Chemicals, Milwaukee, Wis.) was added and the mixture stirred at room temperature overnight. Silica gel was added to the reaction mixture and the mixture evaporated. The residue was purified by silica gel column chromatography (2×20 cm) using a gradient of MeOH/$CH_2Cl_2$ (10–40%, v/v) as eluent. The fractions containing the desired product were combined and evaporated to provide 80 mg of product (80% yield).

EXAMPLE 8

Synthesis of Theophylline-F 238 mg of amino-theophylline (1 mmole) was dissolved in 5 ml of dry DMF containing 200 µl of triethylamine. 389 mg of fluorescein isothiocyanate (isomer I) (1 mmole) was dissolved in 750 µl of dry DMF, then this solution added to the first. The reaction mixture was stirred at room temperature overnight. The solvent of the reaction mixture was removed to dryness. The residue was taken up with methanol and 1 g of silica gel was added. The methanol was removed, leaving an orange powder which was applied to silica gel column chromatography using $CH_2Cl_2$/MeOH (80/20, v/v) as eluent.

The product was obtained in 69.4% yield (435.5 mg).

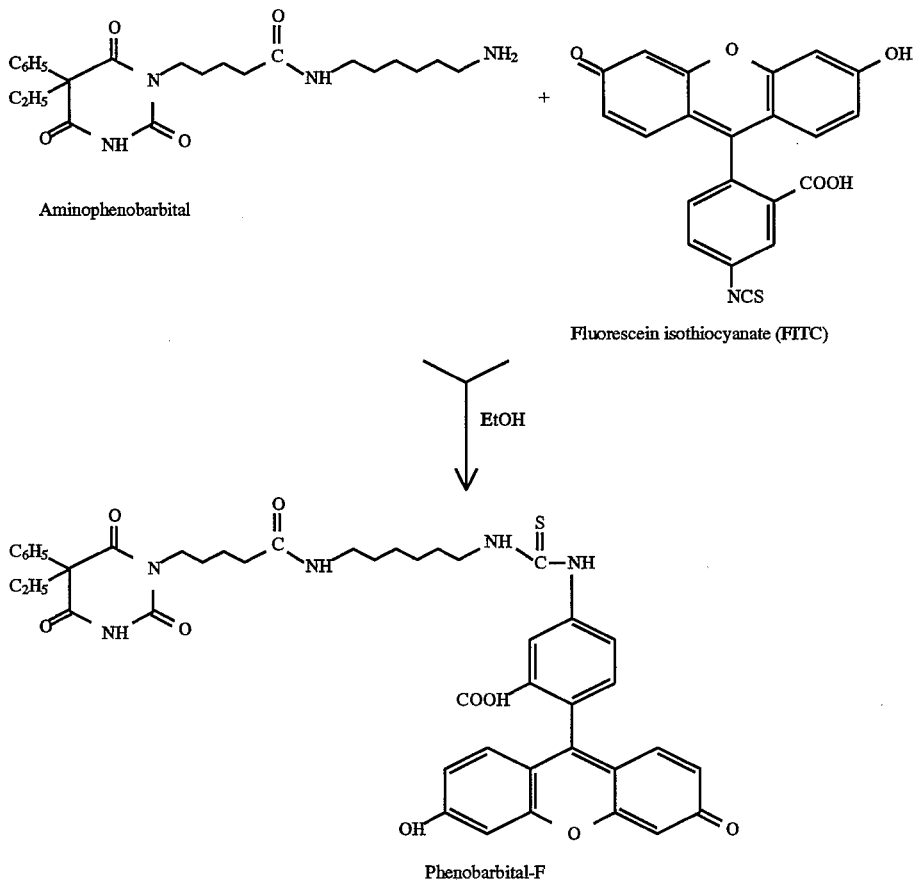

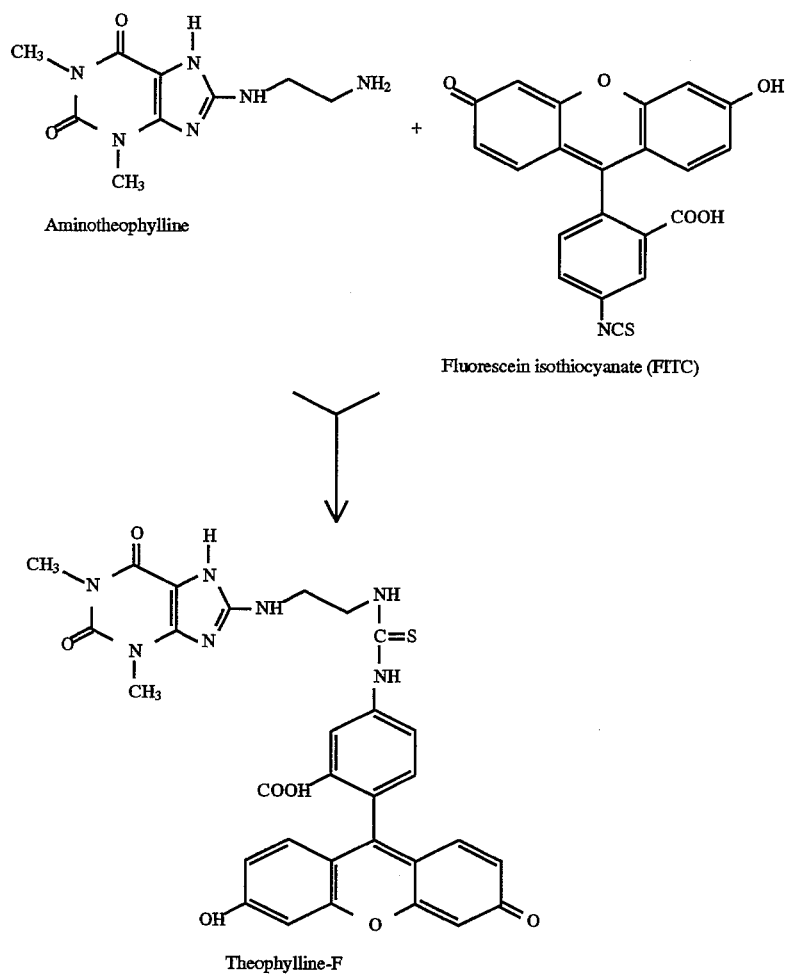

EXAMPLE 9

Phenobarbital Single Analyte Immunoassay using Heteroprocessor

A heteroprocessor is a device in which the movement of a series of syringe plungers is controlled in specific temporal sequences. A series of special piper tips, with polyethylene filters at one end to hold the solid support in place, were attached to the syringes. When the plungers move up, liquid is pulled through the pipet tips and contacts the solid support. The volume of liquid passing through the tips can be changed from 50 µl to 500 µl; typically, the device is set for 100 µl. When the plungers move down, liquid is pushed out of the tips back into the sample cups.

The following oligonucleotide sequences were employed:

5' CAAAATACGTGGCCTTATGGTTACAG 3'    (SEQ ID NO:1)
5' AAGGCCACGTATTTTGCAAGCTATTTAACT 3'    (SEQ ID NO:2)
5' AGTTAAATAGCTTGCAAAATACGTGGCCTT 5'    (SEQ ID NO:3).

The assay was designed as follows:

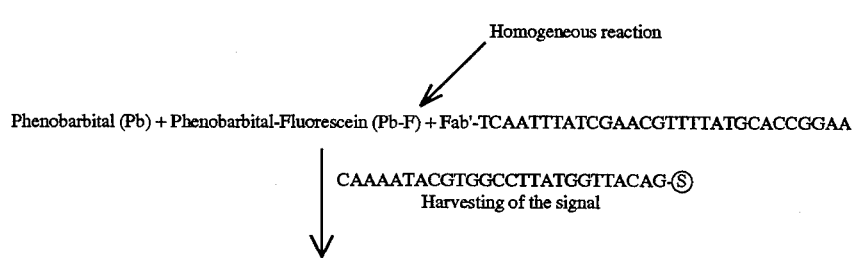

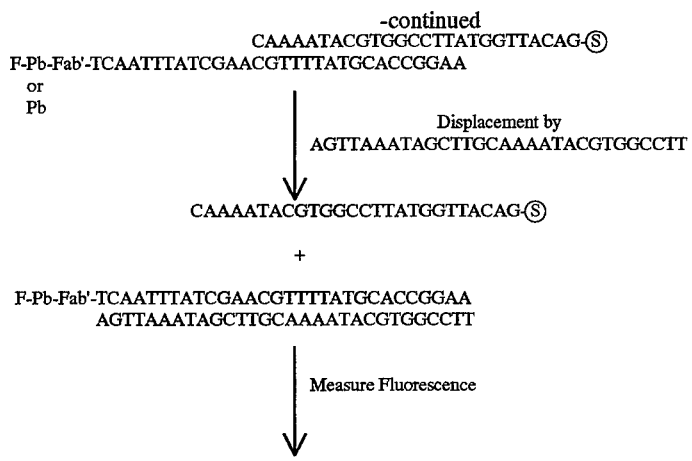

Incubation was carried out in a series of sample cups (available from Beckman Instruments) by adding 20 μl of samples or standards (calibrators) to 500 ng of Pb-F and 0.05 $Abs_{280}$ of Pb-Fab'-oligonucleotide in each cup. (Pb-Fab'-oligonucleotide is an Fab' fragment of antibody to phenobarbital conjugated with oligonucleotide.) The samples were incubated for 5 minutes at room temperature.

Harvesting was effected by placing the sample cups under the heteroprocessor tips containing 5 μl of packed Fractogel-oligonucleotide (Pb sequence SEQ ID NO:1) and raising the cups so that the tips were dipped in the solutions. The harvesting step was carried out by repetitive up and down motions for 15 minutes. The sample cups were then removed and the tips washed 2 times with 1M NaCl.

Displacement was effected by pipetting 1 Abs260 of Pb-displacer (SEQ ID NO:3) in 200 μl of 1M NaCl into each empty cup and placing the cups under the tips. After 3 minutes contact between the support and the displacer, the cups were removed. 100 μl of solution was pipetted out of each cup, diluted with 1.9 ml of 0.1M Tris pH=7.5 and mixed well. Fluorescence was then measured using a luminescence spectrometer ($\lambda_{ex}$=480; $\lambda_{em}$=520).

To clean up and prepare the solid support for another assay, 200 μl of 7M urea was introduced into a new cup, the heteroprocessor was run for 10 minutes and the support then washed 5 times with 1M NaCl.

The results of the assay are reported in Table 4.

TABLE 4

| Pb std | 0 std μg/ml | 5 std μg/ml | 10 std μg/ml | 20 std μg/ml | 40 std μg/ml | 80 std μg/ml |
|---|---|---|---|---|---|---|
| Fluorescence reading | 54.2 | 44.5 | 38.5 | 29.6 | 20.7 | 14.0 |

EXAMPLE 10

Phenobarbital Immunoassay using Flow-through System

This example illustrates carrying out the method of the present invention in an automated flow-through system in which the flow of a pressurized liquid is controlled through the mechanism of opening or closing a set of solenoid valves. The liquid then goes through a column containing a solid support, where immunoreaction in accordance with the present invention takes place. The outlet is connected to a three-way valve, where the liquid can be diverted either to a fraction collector or to a waste collector.

To carry out the assay of the present invention using the flow-through system, Pb-displacer (SEQ ID NO:3) (1 $Abs_{260}$/assay), wash solution (1M NaCl) and clean-up buffer (7M urea) each was attached to separate solenoid valves. Blue buffer (50% fetal calf serum in 0.1M tris, 0.6M sodium citrate; 250 μl/assay) was mixed with Pb-FITC (500 ng/assay), Pb-standards (0, 5, 10, 20, 40 and 80 μg/ml) and Pb-Fab'-oligonucleotide (0.05 $Abs_{280}$/assay) in a small Teflon tube and the mixture incubated for 5 minutes at room temperature. The tube was attached to a solenoid valve. The program was then initiated. First, the complex was delivered through the column. After 15 minutes, the solid support was washed with wash solution. Pb-displacer was then delivered, and after 2 minutes samples were collected through the fraction collector outlet. Clean-up buffer was introduced for 10 minutes to completely clean the support. Finally, the solid support was washed for 2 minutes, leaving it ready for the next assay.

The results are reported in Table 5.

TABLE 5

| Pb-std μg/ml | 0 | 5 | 10 | 20 | 40 | 80 |
|---|---|---|---|---|---|---|
| Fluorescence reading | 37.8 | 28.2 | 23.7 | 17.6 | 12.7 | 10.1 |

EXAMPLE 11

Phenobarbital Assay Using Robotic Work Station

This example demonstrates carrying out the method of the present invention using a robotic work station. One such system (available from Beckman Instruments under the trade designation Biomek™) is an automated laboratory work station in which the tasks of pipetting, delivering and mixing reagents are completely controlled and automated ["Biomek 1000 Automated Laboratory Workstation," Beckman Instruments, Inc., Fullerton, Calif. (1989)]. In order to run immunoassays using the method of the present invention on a Biomek, a round piece of polyethylene filter was cut and pushed inside a pipet tip to hold the solid support in the pipet. To eliminate foaming during mixing of reagents, a 1:250 dilution of antifoam 2410 (Dow Corning) was added to blue buffer (50% fetal calf serum in 0.1M Tris, 0.6M sodium citrate). For convenience, a plate containing 24 1.5 ml centrifuge tubes was employed in this example; other arrangements (e.g., a 96-well microtiter plate) could also advantageously be used with this apparatus.

The microfuge tubes were arranged as follows:

| | |
|---|---|
| Tube A1: | Blue buffer + standard or sample (250 µl per assay); |
| Tube A2: | Fluorescence label (Pb-F or Theo-F) 100 µl; |
| Tube A3: | Antibody conjugated to oligo (Pb-Fab'-oligonucleotide or Theo-Fab'-oligonucleotide) 100 µl; |
| Tubes A5 and A6: | 1 M NaCl for wash (1 ml each); |
| Tube B1: | Complex mixing tube; |
| Tube B2: | displacement strand 500 µl; |
| Tube B3: | 7 M Urea 750 µl; |
| Tubes B4–B6: | 1 M NaCl for wash (1 ml each). |

The assay sequences were programmed to run in the following manner. First, 250 µl of solution was taken from tube A1 and delivered to B1. 100 µl of solution was taken from tube A2 and delivered to B1. 100 µl of solution was taken from tube A3 and delivered to B1. The contents of the tube were mixed and held for 5 minutes. Harvesting was then effected for 15 minutes by pumping the contents of tube B1 repeatedly up and down in the pipet tip containing the solid support. The support was washed with solution from tubes A5 and A6. Displacement was effected with the displacement agent in tube B2 for 3 minutes (with mixing). The duplex was then cleaved in tube B3 for 10 minutes (with mixing). Finally, the solid support was washed for reuse in tube B4, B5 and B6.

A phenobarbital standard curve was established with the results obtained using above set up. The results are reported in Table 6.

TABLE 6

| Pb-std µg/ml | 0 | 5 | 10 | 20 | 40 | 80 |
|---|---|---|---|---|---|---|
| Fluorescence reading | 70.5 | 60.5 | 51.5 | 42.2 | 28.5 | 19.8 |

EXAMPLE 12

Theophylline Single Analyte Immunoassay using Heteroprocessor Format

A heteroprocessor is a device in which the movement of a series of syringe plungers are controlled. A series of special pipet tips, with polyethylene filters at one end to hold the solid support in place, were attached to the syringes. When the plungers are moved up, liquid is pulled through the pipet tips and contacts the solid support. The volume of liquid passing through the tips can be varied from 50 µl to 500 µl; typically (as in this experiment the volume is set at 100 µl. When the plungers are moved down, liquid is pushed out of the tips back into the sample cups. Repeated up and down movement of plungers provides very effective contact of the liquids with the solids contained within the tips.

For this experiment, the following oligonucleotide sequences were employed:

| | |
|---|---|
| 5' CGACGAGCGTGACACCACGATGCCTG 3' | (SEQ ID NO:7) |
| 5' GGTGTCACGCTCGTCGTTTGGTATGGCTTC 5' | (SEQ ID NO:8) |
| 5' GAAGCCATACCAAACGACGAGCGTGACACC 3' | (SEQ ID NO:9). |

The assay was designed as follows:

5'CGACGAGCGTGACACCACGATGCCTG3'--Gel
(Theo)Fab'--3'CTTCGGTATGGTTTGCTGCTCGCACTGTGG5'
5'GAAGCCATACCAAACGACGAGCGTGACACC3':Displacer Incubation is effected in a series of sample cups (Synchron) by adding 100 µl of samples or standards (calibrators) to 125 ng of Theo-FITC and 0.03 Abs$_{280}$ of Theo-Fab'-oligonucleotide (an Fab' fragment of antibody to theophylline conjugated to oligonucleotide) in each cup and incubating the mixtures for 5 minutes at room temperature.

For harvesting, the sample cups were placed under heteroprocessor tips that contained 10 µl of packed Fractogel-oligonucleotide (Theo sequence SEQ ID NO:7) and the cups raised so that the tips were dipped in the solution. The harvesting step was run for 15 minutes. The sample cups were then removed and tips were washed 2 times with 1M NaCl.

Displacement was carried out by pipetting 1 Abs$_{260}$ of Theo-displacer (SEQ ID NO:9) in 200 µl of 1M NaCl into each empty cup and placing the cups under the tips. The heteroprocessor program was run for 3 minutes, then the cups removed. 100 µl of solution was pipetted out of each cup and diluted with 1.9 ml of 0.1M Tris pH=7.5. After thorough mixing, fluorescence was measured using a luminescence spectrometer ($\lambda_{ex}$=493; $\lambda_{em}$=515).

To clean up and prepare the solid support for another assay, 200 µl of 7M Urea was pipetted into a new cup and the heteroprocessor program was run for 10 minutes. The support was then washed 5 times with 1M NaCl.

The results are reported in Table 7.

TABLE 7

| Theo std | 0 std µg/ml | 2.5 std µg/ml | 5 std µg/ml | 10 std µg/ml | 20 std µg/ml | 40 std µg/ml |
|---|---|---|---|---|---|---|
| Fluorescence reading | 38.6 | 33.0 | 31.0 | 27.0 | 22.0 | 14.6 |

EXAMPLE 13

Immobilization of Oligonucleotide on Membrane

Oligonucleotide-NH$_2$(100 Abs$_{260}$/2 ml) was dissolved in coupling buffer (0.5M potassium phosphate pH 7.5). A 1×10 cm strip of Immobilon AV membrane (commercially available from Millipore, Bedford, Mass.) was placed in the oligo solution and rocked at room temperature overnight. Unreacted groups on the membrane were capped by incubating the membrane in 10 ml of capping solution (monoethanolamine, 10% (v/v) in 1.0M sodium bicarbonate, pH 9.5) for 2 hours at room temperature with agitation.

The membrane was washed with 10 ml of washing solution (0.1% Tween-20 in PBS 1×) for 30 minutes with agitation to remove excess uncoupled ligand. This step was repeated once. The membrane was then air dried and stored at 4° C.

EXAMPLE 14

Immobilization of Oligonucleotide on Membrane through Avidin-Biotin Interaction 75 mg of Avidin was dissolved in 75 ml of coupling buffer (0.5M potassium phosphate pH 7.5). A 4×5 cm strip of Immobilon AV membrane was placed in the avidin solution and rocked at room temperature overnight. Unreacted groups on the membrane were capped by incubating the membrane in 90 ml of capping solution (monoethanolamine, 10% (v/v) in 1.0M sodium bicarbonate, pH 9.5) for 2 hours at room temperature with agitation. The membrane was then washed with 100 ml of washing solution (0.1% Tween-20 in PBS 1×) for 30 minutes with agitation to remove excess of uncoupled ligand. The procedure was repeated once. Then the membrane was treated with succinic anhydride to neutralize the positive charge on the avidin and minimize non-specific binding of oligonucleotides. This was accomplished by air drying the membrane and adding 60 ml of 0.5M phosphate buffer pH 8.0, followed by the dropwise addition of succinic anhydride solution (1.2 g of succinic anhydride in 6 ml of DMF) and shaking for 1 hour at room temperature. The pH was then adjusted to 8.6 with $K_2CO_3$. The solution was shaken for 2 hours at room temperature and stored overnight at 4° C. The membrane was washed 5 times with 1M NaCl, 0.1M Tris pH 7.5 and 0.1% Tween-20 (100 ml/wash) and washed 2 times with 0.1M Tris pH 7.5 (150 ml/wash). The membrane was then air dried and stored at 4° C.

Amino oligonucleotide (30 $Abs_{260}$ in 30 µl of water) was concentrated using a Centricon-3 centrifuge. The oligonucleotide solution was adjusted to 50 mM bicarbonate using 0.5M bicarbonate (10 µl) and to 0.1M NaCl using 1M NaCl (10 µl). 2 mg of Biotin-XX-NHS (available from Clontech Laboratories, Palo Alto, Calif.) was dissolved in 25 µl DMF. The oligonucleotide solution and biotin solutions were mixed and incubated overnight at room temperature. The product was purified on a G-25 DNA grade Sephadex column and eluted with water. The first peak was biotinylated oligonucleotide (about 25 $Abs_{260}$).

60 $Abs_{260}$ of biotinylated oligonucleotide was dissolved in 3 ml of reaction buffer (10 mM Tris pH 7.4, 1 mM EDTA, 50 mM NaCl). The avidin membrane was immersed in the solution and incubated for 3 hours at room temperature. The membrane was washed with 10 ml of reaction buffer (3 times). Then, the membrane was washed with 1M NaCl until absorbance of the washed solution read 0 at 260 nm. The membrane was air dried and stored at 4° C.

EXAMPLE 15

Phenobarbital Immunoassay using Immobilon-AV Membrane on Heteroprocessor

Pb-standards (0, 5, 10, 20, 40 and 80 µg/ml:20 µl/assay), Pb-F (250 ng) and Pb-Fab'-oligo (0.05 $Abs_{280}$) were added to a series of sample cups. The cups were then incubated for 15 minutes at room temperature. The sample cups were then placed under heteroprocessor tips that contained Immobilon-oligo (Pb sequence SEQ ID NO:1; 1 cm², 0.1 $Abs_{260}/cm^2$) and the cups raised so that the tips were dipped in the solutions. The harvesting step was run for 30 minutes. The sample cups were then removed and the tips washed 2 times with 1M NaCl. 1 $Abs_{260}$ of Pb-displacer (SEQ ID NO:3) in 200 µl of 1 M NaCl was pipetted into each empty cups and the cups put under the tips. The program was run for 5 minutes then the cups removed. 100 µl of solution was pipetted out of each cup and diluted with 1.9 ml of 0.1M Tris pH=7.5. After thorough mixing, fluorescence was measured using a luminescence spectrometer ($\lambda_{ex}$=493; $\lambda_{em}$=515).

To clean up and prepare the support for another assay, 200 µl of 7M urea was pipetted into new cups and the heteroprocessor run for 10 minutes. The support was then washed 5 times with 1M NaCl.

The results are reported in Table 8.

TABLE 8

| Pb std | 0 std µg/ml | 5 std µg/ml | 10 std µg/ml | 20 std µg/ml | 40 std µg/ml | 80 std µg/ml |
|---|---|---|---|---|---|---|
| Fluorescence reading | 41.2 | 33.2 | 26.4 | 23.2 | 13.8 | 10.4 |

EXAMPLE 16

Simultaneous Dual Analyte Immunoassay

In this example, simultaneous assays were carried out for phenobarbital and theophylline. The following assay design was employed using the previously-identified sequences attached to the Fractogel solid support (SS) or to antibody or Fab' fragments, and as displacers:

```
                      5' CAAAATACGTGGCCTTATGGTTACAG 3'--SS
(Pb)Fab'--3' TCAATTTATCGAACGTTTTATGCACCGGAA 5'
             5' AGTTAAATAGCTTGCAAAATACGTGGCCTT 3' (Displacer)
```

```
                      5' CGACGAGCGTGACACCACGATGCCTG 3'--SS
(Theo)Fab'--3' CTTCGGTATGGTTTGCTGCTCGCACTGTGG 5'
             5' GAAGCCATACCAAACGACGAGCGTGACACC 3' (Displacer)
```

In a series of capsules, mixtures were prepared of theophylline standards (0, 2.5, 5, 10, 20 and 40 µg/ml; 150 µl), phenobarbital standards (0, 5, 10, 20, 40 and 80 µg/ml; 20 µl), Theo-F (100 ng), Pb-F (250 ng), Theo-Ab-oligo (0.05 $Abs_{280}$) and Pb-Fab'-oligo (0.05 $Abs_{280}$). The mixtures were incubated at 37° C. for 3 minutes with continuous shaking. Harvesting was effected by adding Fractogel-oligonucleotide (Pb) (SEQ ID NO:1) (5 µl packed volume) and Fractogel-oligonucleotide (Theo) (SEQ ID NO:7) (10 µl packed volume) supports to each capsule and shaking for 5 minutes at 37° C. All of the liquid was blown out and the solid support washed 3 times with 1M NaCl, which was then blown out. To displace the complexes from the solid support, the Theo-displacer strand (SEQ ID NO:9) (1 $Abs_{260}$ in 1M NaCl) was added and the mixture shaken for 2 minutes at 37° C. The liquid was blown out in a test tube for fluorescence measurement. The solid support was washed 2 times with 1M NaCl (which was then blown out). The Pb-displacer strand (SEQ ID NO:3) (1 $Abs_{260}$ in 1M NaCl) was then added and the mixture shaken for 2 minutes at 37° C. The liquid was then blown out in a test tube for fluorescence measurement. To prepare the solid support for reuse, 200 µl of 7M Urea was added in each capsule, the mixture shaken for 15 minutes at 37° C. and the liquid blown out. The solid support was then washed 6 times with 1M NaCl to prepare the solid support for another assay.

The results are reported in Table 9.

TABLE 9

| Capsule # | 1 | 2 | 3 | 4 | 5 | 6 |
|---|---|---|---|---|---|---|
| Theo-std, µg/ml | 5 | 20 | 10 | 2.5 | 0 | 40 |
| Pb-std, µg/ml | 10 | 5 | 0 | 80 | 40 | 20 |
| Theo-displacement | 44.3 | 33.8 | 42.3 | 49.4 | 52.7 | 26.3 |
|  | 43.8 | 33.6 | 42.9 | 47.3 | 52.8 | 25.9 |
|  | 45.6 | 33.9 | 43.1 | 47.7 | 51.9 | 25.7 |
| Coefficient of variation (CV) | 1.7 | 0.4 | 0.8 | 1.9 | 0.8 | 0.9 |
| Pb-displacement | 9.7 | 13.6 | 23.9 | 4.0 | 5.2 | 6.1 |
|  | 9.6 | 12.9 | 24.5 | 3.8 | 4.9 | 5.9 |
|  | 10.3 | 13.3 | 23.5 | 3.8 | 5.0 | 6.4 |
| CV | 3.1 | 2.1 | 1.7 | 2.4 | 2.5 | 3.3 |

EXAMPLE 17

Simultaneous Triple Analyte Immunoassay

In a series of capsules, mixtures were prepared of the following: Theophylline standards (0, 2.5, 5, 10, 20 and 40 µg/ml; 150 µl); phenobarbital standards (0, 5, 10, 20, 40 and 80 µg/ml; 20 µl); TSH standards (0, 0.25, 1, 5, 15 and 50 uIU/ml; 200 µl); Theo-F (100 ng); Pb-F (250 ng); TSH-Ab1-HRP (100 µl); Theo-Ab-oligonucleotide SEQ ID NO:8) conjugate (0.05 Abs$_{280}$); Pb-Fab'-oligonucleotide (SEQ ID NO:2) conjugate (0.05 Abs$_{280}$); and TSH-Ab$_2$-oligonucleotide (SEQ ID NO:5) conjugate (0.01 Abs$_{280}$). The mixtures were incubated at 37° C. for 1 hour with continuous shaking. For harvesting, Fractogel-oligonucleotide supports (SEQ ID NO:1, SEQ ID NO:7, SEQ ID NO:4, respectively) (Pb, 5 µl packed volume; Theo, 10 µl packed volume; and TSH, 5 µl packed volume) were added to each capsule; the capsules were then shaken for 15 minutes at 37° C. All the liquid was blown out and the solid support washed 3 times with 1M NaCl, which was then blown out. For displacing, first TSH-displacer strand (SEQ ID NO:6) (1 Abs$_{260}$:200 µl in 1M NaCl) was added and the tube shaken for 2 minutes at 37° C. The liquid was blown out into a test tube; 100 µl was pipetted out for color development (using OPD as substrate) and absorbance measured. The support was then washed 2 times with 1M NaCl, which was blown out. Next, the Theo-displacer strand (SEQ ID NO:9) (1 Abs$_{260}$ in 1M NaCl) was added and the mixture shaken for 2 minutes at 37° C. The liquid was blown out into a test tube for fluorescence measurement, the support washed 2 times with 1M NaCl and the wash solution blown out. Finally, the Pb-displacer strand (SEQ ID NO:3) (1 Abs$_{260}$ in 1M NaCl) was added and the mixture shaken for 2 minutes at 37° C. The liquid was blown out into a test tube for fluorescence measurement. To clean up the solid supports for reuse, 200 µl of 7M urea was added to each capsule, the contents shaken for 15 minutes at 37° C. and the liquid blown out; the support was then washed 6 times with 1M NaCl to prepare the support for another assay.

The results are reported in Table 10.

TABLE 10

| Capsule # | 1 | 2 | 3 | 4 | 5 | 6 |
|---|---|---|---|---|---|---|
| TSH-std µIU/ml | 0 | 5 | .01 | .25 | 50 | 15 |
| Theo-std µg/ml | 10 | 0 | 40 | 2.5 | 20 | 5 |
| Pb-std µg/ml | 5 | 20 | 0 | 10 | 80 | 40 |
| TSH-disp Absorbance | 0.032 | 0.187 | 0.038 | 0.088 | 2.144 | 0.678 |
| Pb-disp Fluorescence | 18.8 | 10.8 | 35.2 | 15.4 | 5.7 | 7.8 |
| Theo-disp Fluorescence | 38.4 | 55.7 | 25.5 | 50.6 | 34.4 | 47.5 |

All standard curves obtained were similar to the standard curves obtained with single analyte. The TSH assay was a sandwich assay, while the phenobarbital and theophylline assays used a competitive assay format. This example thus demonstrates that the inventive method works well with both sandwich and competitive assays, individually or in combination.

EXAMPLE 18

Reusability of Solid support in Dual Analyte Assay

This example demonstrates the reusability of the solid supports through several cycles of a dual assay for phenobarbital (Pb) and theophylline (Theo).

The following sequences were employed bound to the solid support (SS) or Fab' fragments, or as displacement strands:

```
                        5' CAAAATACGTGGCCTTATGGTTACAG 3'--SS
(Pb)Fab'--3' TCAATTTATCGAACGTTTTATGCACCGGAA 5'
              5' AGTTAAATAGCTTGCAAAATACGTGGCCTT 3' (Displacer)
```

```
                         5' CGACGAGCGTGACACCACGATGCCTG 3'--SS
(Theo)Fab'--3' CTTCGGTATGGTTTGCTGCTCGCACTGTGG 5'
              5' GAAGCCATACCAAACGACGAGCGTGACACC 3' (Displacer)
```

The following were mixed in a series of capsules: theophylline standard (2.5 µg/ml: 150 µl); phenobarbital standard (10 µg/ml: 20 µl); Theo-F (100 ng); Pb-F (250 ng); Theo-Ab-oligo conjugate (0.05 Abs$_{280}$); and Pb-Fab'-oligo conjugate (0.05 Abs$_{280}$). The mixtures were incubated at 37° C. for 3 minutes with continuous shaking. For harvesting, Fractogel-oligo sequences (5 µl packed volume Pb sequence and 10 µl packed volume Theo sequence) were added to each capsule and the capsules shaken for 5 minutes at 37° C. All liquid was blown out; the solid support was washed 3 times with 1M NaCl, which was then also blown out. For displacing, the Theo-displacer strand (1 Abs$_{260}$ in 1M NaCl) was added and the mixture shaken for 2 minutes at 37° C. The liquid was then blown out in a test tube for fluorescence measurement. The support was then washed 2 times with 1M NaCl, and the liquid blown out. The Pb-displacer strand (1 Abs$_{260}$ in 1M NaCl) was added and the mixture shaken for 2 minutes at 37 ° C. The liquid was then blown out into a test tube for fluorescence measurement. To prepare the supports for reuse, 200 µl of 7M urea was added to each capsule, the capsules shaken for 15 minutes at 37° C. and the liquid blown out. The support was then washed 6 times with 1M NaCl to prepare the solid support for another assay.

TABLE 11

|  | Pb-displacement | Theo-displacement |
|---|---|---|
| 1st run | 11.6 | 64.7 |
|  | 11.8 | 62.1 |
|  | 11.7 | 65.8 |
| Coefficient of Variation (CV) | 0.70 | 2.42 |
| 2nd run | 11.4 | 62.8 |
|  | 11.5 | 61.4 |
|  | 11.7 | 62.3 |
| CV | 1.08 | 0.93 |
| 3rd run | 11.1 | 58.4 |
|  | 11.2 | 60.2 |
|  | 11.4 | 56.8 |
| CV | 1.11 | 2.38 |
| 4th run | 11.2 | 61.1 |
|  | 11.2 | 60.4 |
|  | 11.5 | 58.7 |
| CV | 1.25 | 1.68 |
| 5th run | 10.9 | 62.7 |
|  | 11.0 | 61.5 |
|  | 10.9 | 61.3 |
| CV | 0.43 | 1.00 |
| 6th run | 11.3 | 58.6 |
|  | 11.6 | 58.1 |
|  | 11.5 | 57.8 |
| CV | 1.09 | 0.57 |
| 7th run | 11.3 | 59.2 |
|  | 11.4 | 59.5 |
|  | 11.4 | 58.7 |
| CV | 0.41 | 0.56 |
| 8th run | 11.3 | 61.6 |
|  | 11.6 | 59.8 |
|  | 11.4 | 62.3 |
| CV | 1.09 | 1.72 |
| 9th run | 10.8 | 63.1 |
|  | 10.6 | 62.7 |
|  | 10.5 | 62.3 |
| CV | 1.17 | 0.52 |
| Overall CV | 2.88 | 3.52 |

As can be seen from the above results, the supports of the present invention can be reused in multiple assays without significant diminution in their effectiveness.

EXAMPLE 19

Simultaneous Analysis of Multiple Analytes using Oligonucleotide Arrays

Oligonucleotides (2 μl volume containing 1 Abs$_{260}$) are spotted onto a nylon membrane in distinct areas. After a few minutes, the oligonucleotides are cross-linked to the membrane using UV light. After washing the membrane in 0.1M Tris buffer (pH 7.5), the membrane containing arrays of oligonucleotides is prepared to harvest signals from a homogeneous reaction mixture.

Homogeneous reaction is performed as described in Example 16 by reacting the serum sample containing various analytes, analyte-fluorescein conjugates and the corresponding antibody-oligonucleotide conjugates. The nylon membrane containing the oligonucleotides is brought into contact with the homogeneous reaction in an incubator for 5 minutes at 37° C. The membrane is then washed with 1M NaCl and the membrane dried using blotting paper.

The membrane is placed on a black plastic plate, covered with 0.1M Tris buffer (pH 7.5) and the fluorescence on the individual spots measured using a CCD camera.

EXAMPLE 20

Immunoassays using Optical Fibers

Quartz rods (1×60 mm) are derivatized with an amine group using 3-aminopropyltriethoxysilane in toluene at 50° C. The amine-derivatized fibers are then succinylated by treatment with 1M succinic anhydride in dichloromethane containing 0.01M N,N-dimethylaminopyridine. The amino oligonucleotide is coupled to the carboxyl group on the quartz rod using water-soluble carbodiimide [Wang, supra, p. 195]. Ethanolamine is used to block the remaining active sites for amines.

After performing homogeneous immunoreaction as described in the previous examples, the fluorescent signal is harvested onto the optical fibers and the bound fluorescence measured using a fiber optic waveguide detector. After measurement, the fiber is washed with 7M urea to dissociate the oligonucleotide duplex, thereby regenerating the fiber to make it ready for reuse. With an evanescent wave type of sensor, it is generally possible to make the measurement without removing or washing the off the solution from which the labeled species has been harvested. The subsequent dissociation step prepares the sensor for re-use, which has generally not been possible with existing fiber optic sensors.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. An assay system for an analyte, comprising:

a first immunoreagent for the analyte comprising a first immunoreactant which binds to the analyte and a first oligonucleotide sequence attached to the first immunoreactant;

a second immunoreagent for the analyte comprising a second immunoreactant which binds to the analyte and a detectable label attached to the second immunoreagent; and a second oligonucleotide sequence complementary to the first oligonucleotide sequence, the second oligonucleotide being bound to a support.

2. A method for determining concentration of an analyte, comprising:

(a) providing a solution of a first immunoreagent for the analyte comprising a first immunoreactant which binds to the analyte and a first oligonucleotide sequence attached to the first immunoreactant, and a second immunoreagent for the analyte comprising a second immunoreactant which binds to the analyte and a label attached to the second immunoreagent;

(b) bringing the analyte in contact with the solution thereby forming an immunoconjugate;

(c) contacting the solution with a solid support to which is bound a second oligonucleotide sequence complementary to the first oligonucleotide sequence under conditions suitable for hybridization of the first and the second oligonucleotide sequences, thereby forming duplexes; and (d) determining the concentration of label contained in the duplexes, to provide the concentration of analyte.

3. A method according to claim 2 wherein said solid support is an optical fiber.

4. A method according to claim 2 wherein step (d) is performed by measuring the label using a fiber optic waveguide detector.

5. A method according to claim 2 further including the steps:

(e) dissociating the hybridized first and second oligonucleotide sequences; and (f) repeating steps (a), (b), and (c).

6. A method according to claim 2, wherein steps (a) and (b) are carried out simultaneously.

7. A method according to claim 2, wherein step (a) precedes step (b).

8. A method according to claim 2, wherein step c) precedes step b) and step b is performed while the solution is in contact with the solid support.

9. A method according to claim 2, wherein the concentration of label is determined without dissociating the duplex.

10. A method according to claim 2, wherein the duplex is dissociated prior to determining the concentration of label.

11. A method according to claim 10, wherein the duplex is dissociated using a cleaving reagent selected from the group consisting of ionized water, urea solutions and formamide solutions.

12. A method according to claim 10, wherein the duplex is dissociated by competitive binding of a displacement agent corresponding in sequence to one of the first and second oligonucleotide sequences.

13. A method according to claim 12, wherein the displacement agent corresponds in sequence to the first oligonucleotide.

14. A method according to claim 12, wherein the displacement agent corresponds in sequence to the second oligonucleotide.

15. A method according to claim 2, further comprising dissociating the duplex by competitive binding of a displacement agent, the displacement agent comprising a sequence complementary to the second oligonucleotide sequence.

16. An assay system for an analyte, comprising:
an immunoreagent for the analyte comprising a first immunoreactant which binds specifically to the analyte and a label attached to the first immunoreactant;
an analyte competitor which competes with free analyte for binding to the immunoreagent, the analyte competitor having a first oligonucleotide sequence bound thereto; and
a second oligonucleotide sequence complementary to the first oligonucleotide sequence, the second oligonucleotide being bound to a support.

17. An assay system according to claim 16, wherein the analyte competitor is an analog of the analyte which binds specifically to the immunoreactant with first oligonucleotide sequence bound thereto.

18. A method for determining concentration of an analyte, comprising:
(a) reacting the analyte in a solution phase with an immunoreagent for the analyte comprising an immunoreactant which binds specifically to the analyte and a label attached to the immunoreactant to form an immunoconjugate, said solution further containing an analyte competitor and a first oligonucleotide sequence bound thereto, wherein the analyte competitor competes with free analyte for binding to the immunoreagent;
(b) contacting the solution with a solid support to which is bound a second oligonucleotide sequence complementary to the first oligonucleotide sequence under conditions suitable for hybridization of the first and the second oligonucleotide sequences, thereby forming duplexes;
(c) determining the concentration of label contained in the duplexes; and
(d) comparing the determined concentration to a concentration obtained by binding analyte competitor and first nucleotide sequence in absence of analyte, to provide the concentration of analyte.

19. An assay system for an analyte, comprising:
an immunoreagent for the analyte comprising a first immunoreactant which binds specifically to the analyte and a first oligonucleotide sequence attached to the immunoreactant;
an analyte competitor which competes with free analyte for binding to the immunoreagent and a label bound thereto; and
a second oligonucleotide sequence complementary to the first oligonucleotide sequence, the second oligonucleotide being bound to a support.

20. A method for determining concentration of an analyte, comprising:
(a) reacting the analyte in a solution phase with an immunoreagent for the analyte wherein the immunoreagent comprise an immunoreactant which binds specifically to the analyte and a first oligonucleotide sequence attached to the immunoreactant, to form an immunoconjugate, said solution further containing an analyte competitor and a label bound thereto, wherein the analyte competitor competes with free analyte for binding to the immunoreagent;
(b) contacting the solution with a solid support to which is bound a second oligonucleotide sequence complementary to the first oligonucleotide sequence under conditions suitable for hybridization of the first and the second oligonucleotide sequences, thereby forming duplexes;
(c) determining concentration of label contained in the duplexes; and
(d) comparing the determined concentration to a concentration obtained by binding analyte competitor and immunoreagent in absence of analyte, to provide the concentration of analyte.

21. An assay system for an analyte, comprising:
an immunoreagent for the analyte comprising a first immunoreactant which binds specifically to the analyte and a first oligonucleotide sequence attached to the immunoreactant and
a second oligonucleotide sequence complementary to the first oligonucleotide sequence, the second oligonucleotide being bound to a support.

22. A method for determining the presence of an analyte in a sample, comprising:
(a) reacting the sample in a solution phase with an immunoreagent for the analyte comprising an immunoreactant which binds specifically to the analyte and a first oligonucleotide sequence attached to the immunoreactant, to form an immunoconjugate;
(b) contacting the solution with a solid support to which is bound a second oligonucleotide sequence complementary to the first oligonucleotide sequence under conditions suitable for hybridization of the first and the second oligonucleotide sequences, thereby forming duplexes which harvest the immunoconjugate from the solution; and
(c) determining analyte contained in the duplexes.

23. A composition of matter comprising:
an antibody or fragment thereof which binds an analyte;
a first oligonucleotide;
a linking agent attaching the antibody or fragment thereof to the first oligonucleotide; and
a second oligonucleotide having an attachment means for linking the second oligonucleotide to a solid support.

24. A method for simultaneously determining multiple analytes, comprising:
(a) bringing the analytes into contact with multiple first immunoreagents, each immunoreagent comprising a first immunoreactant which binds to a single analyte and a first oligonucleotide sequence attached to the first immunoreactant, and multiple second immunoreagents, each second immunoreagent including a second immunoreactant which binds to a single analyte and a label attached to the second immunoreactant in a solution containing the analytes and first and second immunoreagents, thereby forming multiple immunoconjugates;

(b) contacting the solution with a solid support to which is bound multiple second oligonucleotide sequences, each of the second oligonucleotide sequences being complementary to a corresponding one of the first oligonucleotide sequence, under conditions suitable for hybridization of all of the first oligonucleotide sequences to their corresponding second oligonucleotide sequences, thereby forming duplexes; and (c) detecting label contained in the duplexes, to determine the presence or absence of multiple analytes.

25. A method according to claim 24 further wherein step (c) includes determining the concentration of the labels in the duplexes, thereby determining the concentration of the analytes.

* * * * *